(12) United States Patent
Maclennan et al.

(10) Patent No.: US 6,326,155 B1
(45) Date of Patent: *Dec. 4, 2001

(54) ENGINEERING AFFINITY LIGANDS FOR MACROMOLECULES

(75) Inventors: John Moore Maclennan, Bellingham, MA (US); Robert Charles Ladner, Ijamsville, MD (US)

(73) Assignee: Dyax Corp., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/821,498

(22) Filed: Mar. 21, 1997

Related U.S. Application Data

(63) Continuation-in-part of application No. 08/619,885, filed on Mar. 20, 1995, now abandoned.

(51) Int. Cl.$^7$ .............................. G01N 33/53; C12Q 1/68; A61K 38/16
(52) U.S. Cl. .................. 435/7.1; 435/6; 435/DIG. 1; 435/DIG. 3; 435/DIG. 14; 530/350; 935/66; 935/79; 935/80; 935/76
(58) Field of Search .......................... 435/5, 6, 7.1, 69.1, 435/69.7, 320.1, DIG. 1, DIG. 2, DIG. 3, DIG. 40, DIG. 48, DIG. 34, DIG. 14; 935/66, 73, 76, 79, 80; 530/350

(56) References Cited

U.S. PATENT DOCUMENTS

| | | |
|---|---|---|
| 4,898,825 | 2/1990 | Morii et al. . |
| 5,133,866 | 7/1992 | Kauvar . |
| 5,223,409 * | 6/1993 | Ladner . |
| 5,270,270 * | 12/1993 | Schatz et al. ................. 435/7.35 |
| 5,403,484 | 4/1995 | Ladner et al. . |
| 5,498,538 * | 3/1996 | Kay et al. ...................... 435/69.1 |
| 5,567,317 | 10/1996 | Kauver . |
| 5,658,727 * | 8/1997 | Barbas et al. ................... 435/6 |
| 5,955,358 * | 9/1999 | Huse . |

FOREIGN PATENT DOCUMENTS

97/22617 *  6/1997  (WO) .

OTHER PUBLICATIONS

Ngo and Khatter. Avaid AL a sytheic ligand affinity gel mimiciing immobilized bacterial antibody receptor for purification of immunoglobin G. J. Chromat. 597: 101–109. 1992.*

McCafferty et al. Phage antibodies: filamentous phage display antibody variable domains Nature 348:: 552–554, 1990.*

McCafferty et al. Selection and purification of Murie antibody fragments that bind a transition state analog. App. Biochem. Biotech. 47: 157–173, 1994.*

McClennan. Engineering Microprotein ligands for Large–Scale affity purification. BIO/Technology 13: 1180–1183, 1995.*

Scott et al. Searching for peptide ligands with an epitope library. Science 249: 386–390, 1990.*

Lowman et al. Selectin high affinity binding proteins by monovalent phage display. Biochemistry 30: 10832–10838, 1991.*

Ruddinger, J. Characteristics of the amino acids as components of a peptide hormone sequence. In Pepotide Hormones, University Park Press, Baltimore pp. 1–7, 1976.*

Boschetti, 1994, Advanced sorbents for preparative protein separation purposes, *J. Chromatography A*, 658: 207–236.

Huang et al., 1996, Affinity purification of von Willebrand factor using ligands derived from peptide libraries, *Bioorganic & Medicinal Chem.*, 4(5): 699–708.

Knight, 1990, Bioseparations: media and modes, *Bio/Technology*, 8: 200–201.

Ladner, 1995, Constrained peptides as binding entities, *Trends in Biotechnology*, 13(10): 426–430.

Le Nguyen et al., 1989, Solid phase synthesis of a trypsin inhibitor isolated from the Cucurbitaceae *Ecballium elaterium*, *Int. J. Peptide Protein Res.*, 34: 492–497.

Markland et al., 1995, Selection for protese inhibitors using bacteriophage display, *Methods Enzymol.*, 267: 28–51.

Narayanan, 1994, Preparative affinity chromatography of proteins, *J. Chromatography A*, 658: 237–258.

Scopes, 1982, *Protein Purification: Principles and Practise*, New York, Springer–Verlag, 111–112, 117–125.

Vedvick et al., 1991, High–level secretion of biologically active aprotinin from the yeast *Pichia pastoris*, *J. Industrial Microbiol.*, 7: 197–202.

Wagner et al., 1992, High level expression, purification, and characterization of the Kunitz–type protease inhibitor domain of protease nexin–2/amyloid β–protein precursor, *Biochem. Biophys. Res. Comm.*, 186(2): 1138–1145.

* cited by examiner

Primary Examiner—Padmashri Ponnaluri
(74) Attorney, Agent, or Firm—Leon R. Yankwich; Kenneth P. Zwicker; Ivana Maravic-Magovcevic

(57) ABSTRACT

A method is disclosed for obtaining highly specific and tailored ligands suitable for purifying a particular product target or for eliminating particular target impurities in a feed stream. Engineered affinity ligands according to the invention will bind a target with high specificity at a preselected binding condition and release the target at a preselected elution condition. The ligands are isolated by contacting a target with a multiplicity of polypeptides derived through variegation of the structure of a candidate binding domain, the variants (or analogues) including polypeptides favoring binding to the target under desired binding conditions and release from the target under elution conditions, where the binding and elution conditions differ according to one or more parameters, such as pH, temperature, concentration of salt or volume % of an organic solvent.

10 Claims, 13 Drawing Sheets

ENGINEERING AFFINITY LIGANDS FOR MACROMOLECULES

This application is a continuation-in-part of copending U.S. application Ser. No. 08/619,885 filed Mar. 20, 1996 now abandoned.

FIELD OF THE INVENTION

The present invention relates to the field of purification of biomolecules. Specifically, the present invention relates to discovery of and isolation of affinity ligands for particular target biomolecules. Such affinity ligands will be useful for purification of target biomolecules from solutions under desirable separation conditions.

BACKGROUND OF THE INVENTION

Biomolecules of medical or industrial importance, which may be proteins, glycoproteins, lipoproteins, polysaccharides, lipids or nucleic acids, are produced by a wide variety of methods including chemical synthesis; secretion into culture medium by naturally occurring or recombinantly transformed bacteria, yeasts, fungi, insect cells, and mammalian cells; accumulation in cultured cells (e.g., in inclusion bodies); secretion from genetically engineered organisms (e.g., in the milk of transgenic mammals); and recovery from biological sources such as urine, blood, milk, plant infusions, fungal extracts, and the like. Most biomolecules thus produced are of little use, however, without purification away from other elements (i.e., "impurities") present in the solutions in which they are produced or without concentration of the biomolecule so that it comprises a much larger fraction of the solution.

Chromatography is a dominant purification and concentration technique used in the large-scale isolation of biomolecular targets. With a properly designed series of chromatographic steps, a single biomolecular component can be isolated from a complex mixture with contaminants that range from inorganic salts to incorrectly folded or partially degraded forms of the target macromolecule itself. At the same time, chromatographic purification is a major (and often the largest single) cost in the manufacture of a biomolecule product. Typical biotherapeutic purifications require from two to six or more chromatographic steps, utilizing size-exclusion, ion-exchange, hydrophobic interaction, and affinity chromatographic modes.

While size-exclusion is often used for buffer exchange or as a final step to remove aggregated material, and ion-exchange and hydrophobic interaction are used to concentrate the product and remove major impurities, none of these chromatographies can approach the dramatic singlestep increases in purity achieved using affinity chromatography. Narayanan (1994), for instance, reported a 3000-fold increase in purity through a single affinity chromatography step.

Affinity chromatography is not, however, a commonly used technique in largescale production of biomolecules. The ideal affinity chromatography ligand must, at acceptable cost, (1) capture the target biomolecule with high affinity, high capacity, high specificity, and high selectivity; (2) either not capture or allow differential elution of other species (impurities); (3) allow controlled release of the target under conditions that preserve (i.e., do not degrade or denature) the target; (4) permit sanitization and reuse of the chromatography matrix; and (5) permit elimination or inactivation of any pathogens. However, finding high-affinity ligands of acceptable cost that can tolerate the cleaning and sanitization protocols required in pharmaceutical manufacturing has proved difficult (see, Knight, 1990).

Although far from ideal, dyes (such as cibachron blue) and proteins of known affinity (such as Protein A) have been employed extensively in affinity chromatography. These materials, however, cannot be adapted to new targets and therefore lack the flexibility to be more widely used.

Murine monoclonal antibodies (MAbs) also have been used as affinity ligands. MAbs can be readily generated, and new MAb ligands specific for a new target molecule can be obtained, giving MAb technology a degree of flexibility to meet the individual requirements of a particular manufacturer. Monoclonal antibodies, on the other hand, are not without drawbacks in the field of affinity chromatography: MAbs are expensive to produce, and they are prone to leaching and degradation under the cleaning and sanitization procedures associated with purification of biomolecules, leading MAb-based affinity matrices to lose activity quickly (see, Narayanan, 1994; Boschetti, 1994). In addition, although MAbs can be highly specific for a target, the specificity is often not sufficient to avoid capture of impurities that are closely related to the target. Moreover, the binding characteristics of MAbs are determined by the immunoglobulin repertoire of the immunized animal, and therefore practitioners must settle for the binding characteristics they are dealt by the animal's immune system, i.e., there is little opportunity to optimize or select for particular binding or elution characteristics using only MAb technology. Finally, the molecular mass per binding site (25 kDa to 75 kDa) of MAbs and even MAb fragments is quite high.

Thus, there is a continuing need to develop less expensive, more serviceable and more tailored affinity ligands for particular biomolecular targets. Specifically, there is a need for affinity ligands that more closely approach the characteristics of the ideal affinity ligand described above, that not only bind to a given target molecule with high affinity but also release the target under desirable or selected conditions, that are able to discriminate between the target and other components of the solution in which the target is presented, and/or that are able to endure cleaning and sanitization procedures to provide regenerable, reusable chromatographic matrices.

Such affinity ligands and methods for obtaining them are provided herein.

SUMMARY OF THE INVENTION

The present invention provides methods for obtaining affinity ligands for a particular biomolecular target of interest which exhibit desirable or selected binding properties and release properties. In its broadest aspects, the present invention provides a method for obtaining affinity ligands useful for isolating virtually any target biomolecule from a solution containing it, which ligands may be engineered to exhibit not only favorable binding characteristics for affinity chromatography but also desired release (elution) characteristics and other desired properties such as stability, resistance to degradation, durability, reusability, ease of manufacture, etc.

The present invention also provides a method for obtaining affinity ligands that bind particular impurities (or closely-related groups of impurities) with very high affinity to remove essentially all of that impurity (or impurities) from a solution containing a target. In this case, release of the impurity intact is not important (with respect to purification of the target), but it will be economically advantageous if the affinity matrix containing the ligands can be regenerated and reused.

The present invention also provides a method for isolating affinity ligands capable of binding a particular target under a first specific set of solution conditions and releasing the target under a second specific set of solution conditions.

The present invention thus relates to a method for isolating an affinity ligand suitable for separating a target molecule from a solution containing it without denaturing the target molecule, the method comprising:

(a) selecting, with respect to the target molecule, a first solution condition (i.e., the binding conditions) at which it is desired that an affinity ligand should bind to said target molecule;

(b) selecting, with respect to the target molecule, a second solution condition (i.e., the release conditions) at which it is desired that an affinity complex between said target and said affinity ligand will dissociate and wherein said second solution condition is different from said first solution condition;

(c) selecting a polypeptide candidate binding domain for said target molecule that is stable under both said first and said second solution conditions;

(d) selecting amino acid positions in said candidate binding domain (preferably positions on the surface of the domain, and most preferably close together in the domain) as variable positions;

(e) providing a library of analogues of said candidate binding domain, wherein each analogue differs from said candidate binding domain in the substitution of a different amino acid at one or more of the selected variable amino acid positions;

(f) contacting said library of analogues with the solution containing said target molecule at the first solution condition, for sufficient time to permit analogue/target binding complexes to form;

(g) removing analogues that do not bind under the first solution condition;

(h) altering the conditions of the solution of contacting step (f) to the second solution condition; and (i) recovering the candidate binding analogues released under the second solution condition, wherein the recovered analogues identify isolated affinity ligands.

In certain circumstances, e.g., where the nature of the target molecule is obscure or unknown to the practitioner, or where features involved in the purification of the target (such as the content of the solution in which the target is produced, nature of persistent impurities in the solution, biological activity of the target, production source of the target, etc.) leave doubt as to the range of solution conditions under which the target molecule will remain stable, a preferred method according to the invention for obtaining an affinity ligand suitable for separating the target molecule from the solution containing it will comprise the steps:

(a') ascertaining a range of stability for the target molecule with respect to two or more parameters selected from temperature, pH ionic strength, dielectric constant, concentration of solutes (e.g., concentration of chaotropes, concentration of organic solvents (e.g., methanol, ethanol, acetonitrile, DMSO, DMF, methyl acetate, acetone, methylethylketone, and the like)), and presence or absence of metal ions (e.g., $Zn^{++}$, $Ca^{++}$, $Mg^{++}$) or chelating agents (e.g., EDTA), thereby defining a stability envelope for said target molecule;

(a) selecting, with respect to the target molecule, desired binding conditions within the stability envelope for the target molecule;

(b) selecting, with respect to the target molecule, desired release conditions within the stability envelope for said target molecule, wherein said release conditions are different with respect to at least one parameter from said binding conditions;

(c) selecting a polypeptide candidate binding domain for said target molecule that is stable under both said binding and release conditions;

(d) selecting amino acid positions on the surface of said candidate binding domain as variable positions;

(e) providing a library of analogues of said candidate binding domain (e.g., a phage display library in which a variegated set of polypeptide binding domain analogues is displayed on the surface of bacteriophage), wherein each analogue differs from said candidate binding domain in the substitution of a different amino acid at one or more of the variable amino acid positions designated in step (d);

(f) contacting said library of analogues with the solution containing said target molecule at the binding conditions, for sufficient time to permit analogue/target binding complexes to form;

(g) removing analogues that do not bind the target under the first solution condition;

(h) altering the conditions of the contacting step (f) to the release conditions; and (i) recovering the analogues released under the release condition, wherein the recovered analogues identify isolated affinity ligands.

From the analogues recovered, protein binding domains having the best combination of properties can be selected. Alternatively, additional rounds of selection from additional libraries (steps (e)–(i), above) can be used to enrich the recovery of ligands with those having desirable properties. The practitioner's knowledge of the target, its production and the factors involved in its separation from solution will guide the selection of candidate binding domains, the designation of variable amino acids and the selection of amino acids for substitution at variable positions, to favor the properties desired in the final affinity ligand. Alternatively, if a variegated candidate binding domain library has previously been prepared, the selections steps (c) and (d) need not be repeated, and the practitioner can move directly from selecting binding and release conditions to contacting the library and the target.

It is particularly preferred that the creation of polypeptide analogue libraries for the presentation of a multiplicity of possible affinity binding domains, some of which will bind to the target under binding conditions and release the target under release conditions, make use of techniques for display of analogue proteins on the surface of a genetic package such as a bacteriophage. Such techniques are set forth in U.S. Pat. No. 5,223,409 (Ladner et al.), incorporated herein by reference. By using these powerful techniques, a great number (e.g., $10^7$) of polypeptides of similar structure can be readily produced for use in the methods of this invention.

The affinity ligands prepared according to this invention will be specifically tailored to the separation of a particular target biomolecule. Affinity ligands will thus be obtained in accordance with this invention that have the optimal balance of properties to make them almost ideal affinity ligands for the separation of that particular target, in terms of affinity for binding the target, specificity for the target, release of the target under specified conditions, durability under sanitization conditions, and any other desirable property selected for.

DETAILED DESCRIPTION OF THE PREFERRED EMBODIMENTS

Figure 1:
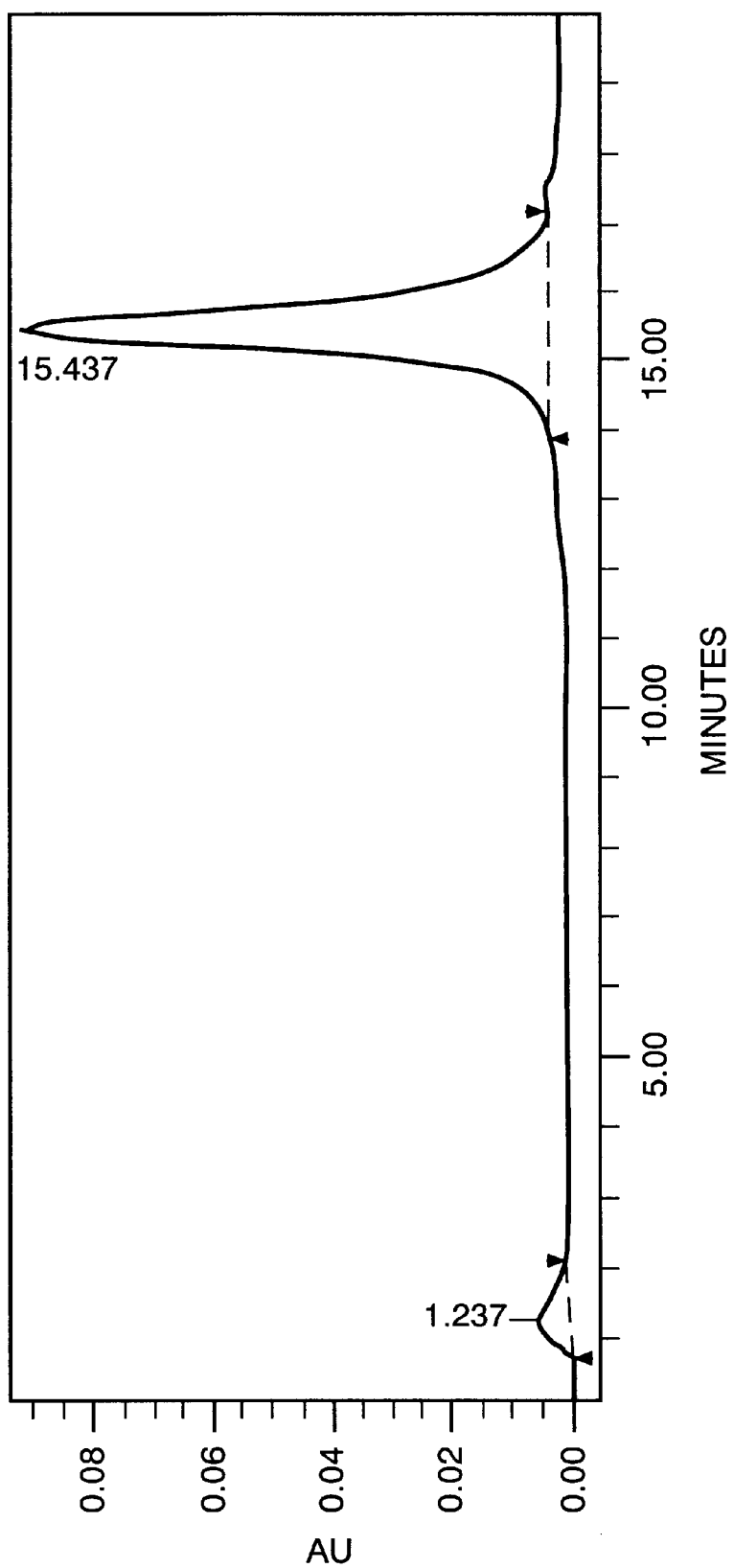
FIG. 1 shows a chromatogram of tissue plasminogen activator or "tPA" (25 μL of 1 mg/mL tPA over an affinity chromatography column having an immobilized tPA affinity ligand (CMTI derivative #109, described in Example 16), with elution over a pH 7–pH 3 gradient. The peak at 15 minutes is estimated to contain approximately 90% of the injected tPA.
Figure 2:
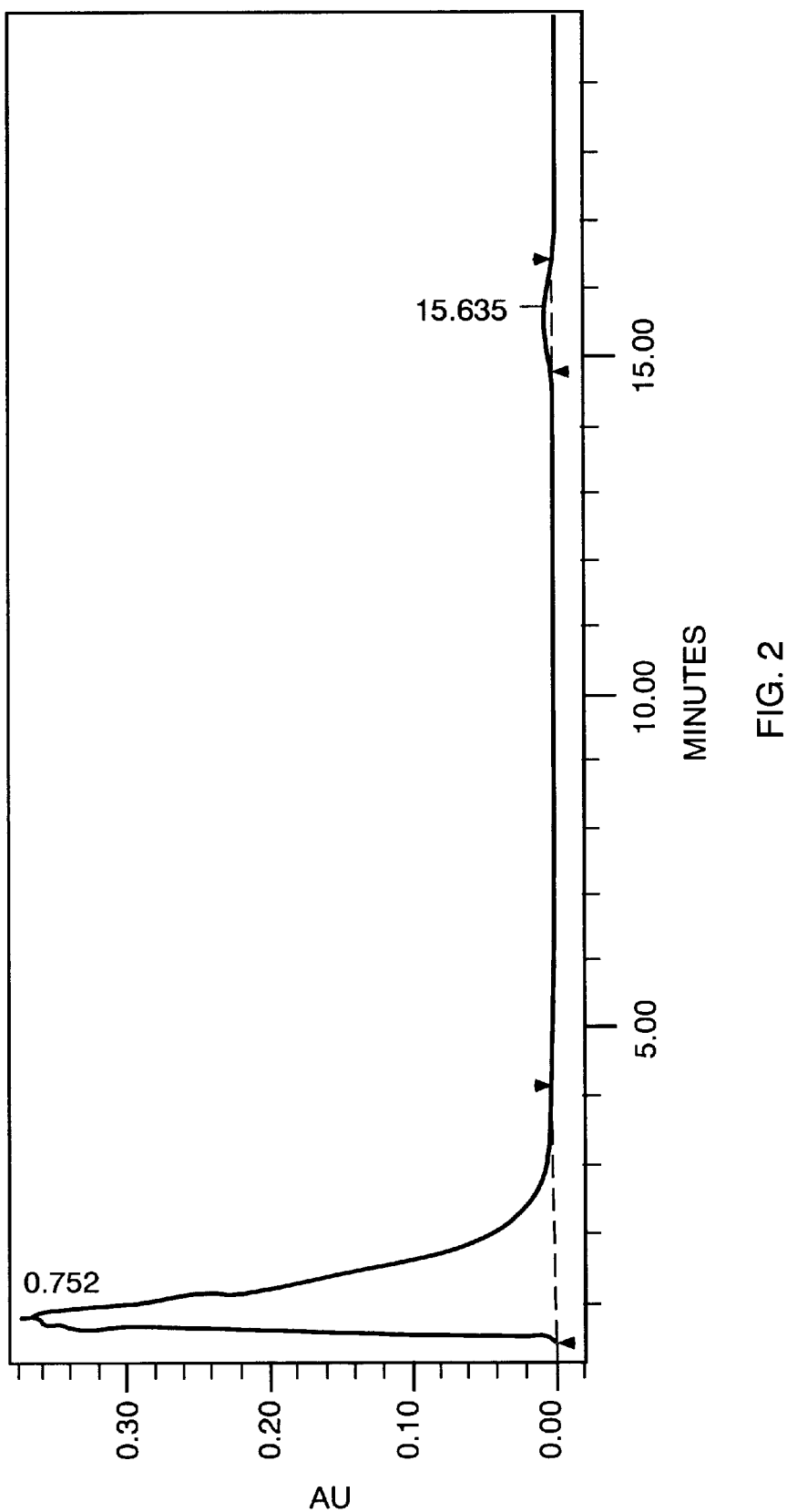
FIG. 2 shows a chromatogram of Coagulation Standard (diluted 10×) over a tPA affinity column (CMTI derivative #109) with elution as described above. The small peak at 15.6 minutes was shown to be a gradient artifact.

The present invention makes possible the efficient purification of target biomolecules by affinity chromatography. As used herein, the term "target" will indicate a particular protein, glycoprotein, lipoprotein, polysaccharide, lipid, lipopolysaccharide, nucleic acids or combinations of molecules from these classes for which a specific ligand is sought. Targets may be active fragments of proteins or may be complexes or aggregates of more than one protein. Targets are not limited to naturally occurring biomolecules; they may be synthetic organic molecules and especially molecules containing one or more chiral centers. A target may exist as part of a larger structure, e.g., as a surface molecule on an organism such as a virus. Indeed, the target may be a cell or a virus particle.

Target biomolecules may be produced in any known way, including chemical synthesis; production in transformed host cells; secretion into culture medium by naturally occurring or recombinantly transformed or transfected bacteria, yeasts, fungi, insect cells, and mammalian cells; secretion from genetically engineered organisms (e.g., transgenic mammals); or in biological fluids or tissues such as urine, blood, milk, etc. The solution that contains the crude target as it is initially produced (i.e., the production solution) will sometimes be referred to as the "feed stream". Although the invention is primarily directed toward recovering target molecules from the solutions in which the target was produced, the invention is not limited to recovery from production feed streams, and affinity ligands developed according to the invention can be used to recover a target from any solution.

Each method of producing a target biomolecule yields the target in a feed stream that contains the target and a number of impurities (with respect to the target). One purpose of the present invention is to produce affinity ligands and preparations (such as chromatography media) comprising such ligands that allow rapid and highly specific purification of targets. Affinity ligands obtained herein bind the target (preferably to the virtual exclusion of any other molecule in the feed stream) with high affinity. Further, the affinity ligands release the target intact and in active form when the solvent conditions are changed. It is important that the release conditions do not adversely affect the target. Preferably, the affinity ligand can bind the target even when it is present at low concentration in the feed stream and release it at high concentration so that one purification step both removes many impurities and concentrates the target. Targets that are to be bound and released in active form will sometimes be referred to as "product targets".

Another aspect of the present invention is to provide affinity ligands that bind particular impurities (or closely-related groups of impurities) with very high affinity to sequester essentially all of that impurity (or those impurities) and thus allow removal of other molecule(s) from it (them). In this case, release of the impurity intact is not important, but it will be economically advantageous if the ligand can be recycled. Targets that are to be captured with maximal affinity but for which release is unimportant are termed "impurity targets".

Characterization of the Target

In the field of purification, almost any fact known or discovered about the target may be used to improve the effectiveness of a purification scheme aimed at isolating it. In practicing the methods of the present invention for obtaining engineered affinity ligands for a target, it is critical to know or to determine solution conditions under which the target is stable, i.e., conditions under which the biomolecule maintains its activity and does not denature. The first steps of the method according to the invention involve selecting a set of conditions in the target purification process at which it is desired that binding to an affinity ligand will take place, and selecting a different set of conditions at which it is desired that binding to the affinity ligand will cease, resulting in release and elution of the target. Both of these conditions must be conditions under which the target is stable, in order that the ligands ultimately obtained have affinity for the intact, active target.

In addition to understanding factors affecting the stability of the target, it is also useful to know other characteristics of the target, such as the concentration of the target in the solution from which it is to be separated, binding or enzymatic activities of the target, the aggregation state of the target (i.e., whether it is a monomer or a multimer), the approximate size (molecular weight) of the target, and the composition of the solution or feed stream containing the target. Such factors will be helpful to the practitioner in selecting (a) binding conditions under which one or more protein ligands would be expected to bind the target, (b) possible changes in conditions that would be likely to make at least some of the protein ligands release the target without denaturing or harming it, and (c) the composition of one or more libraries of potential binding proteins or domains from which suitable ligands can be isolated.

Stability Conditions for the Target

Any biomolecule is stable under some solution conditions, but stability of a target in solution is affected by the conditions of the solution including its temperature, pn ionic strength, dielectric constant and the concentrations of other solutes, such as $[H^+]$, $[Na^+]$, $[Cl^-]$, $[urea]$, $[guadinium^+]$, $[SO_4^-]$, $[HSO_4^-]$, $[PO_4^{--}]$, $[HPO_4^{--}]$, $[H_2PO_4^-]$, $[ClO^-]$, $[NH_4^+]$, $[OH^-]$, $[H_2O_2]$, $[Mg^{++}]$, $[K^+]$, $[Zn^{++}]$, $[Ca^{++}]$, $[Li^+]$, $[NO_3^-]$, [detergent, e.g., Triton X-100], [dodecylsulfate], [glucose], [citrate], [benzoate], [ethanol], [methanol], [acetone], [acetate], [chloroacetate], [dichloroacetate], [trichloroacetate], [formate], [N-methylfromamide], [formamide], [dimethylformamide], [dimethylsulfoxide], [methylethylketone], [methylacetate], EDTA, etc. For each of these parameters and any others known or determined for a particular feed stream, the target will be stable within a range, i.e., within a temperature range, within a pH range, etc. Outside this stability range, the target denatures. Collectively, the ranges of all parameters affecting stability of a particular target determine a "stability envelope" for that feed stream, and the target is expected to remain stable so long as conditions of the solution are maintained within the stability envelope. It is expected that different targets will have different stability envelopes, even in the same feed stream.

The first steps in obtaining affinity ligands suitable for affinity separation of a given target are to select binding conditions and desired release conditions under which the target is stable. If insufficient information regarding stability conditions for a target molecule is known to the practitioner to make a selection of binding conditions, stability conditions can be ascertained either by referring to previous determinations or by determining the stability range with respect to one or more parameters empirically.

It should be noted that it is not necessary to test the stability of the target or determine the full extent of the target's stability envelope in order to select desired binding conditions. The practitioner, based on experience, may simply guess at stability conditions and select a set of binding conditions appropriately. For example, most proteins that have any stability are stable at pH 7, 25° C., and 150 mM NaCl (i.e., pH 7, 25° C., and 150 mM NaCl is usually within the envelope of stability for a given protein). Binding conditions may be selected at pH 7, 25° C., and 150 mM NaCl; and release conditions may be selected in relation to this, by varying one or more of the parameters (e.g., to pH 4, 25° C., and 150 mM NaCl). If either of these conditions is outside the stability envelope of the target, the method will fail to identify any affinity ligands capable of separating the target from a solution, and the method may be repeated, either after determining the stability envelope more accurately or making another guess at where the boundaries of the envelope may lie. As a broader example, very many proteins are stable in a temperature range from 0° C. to 35° C., at a range of pH from pH 8–9 down to pH 4–5, and for [NaCl] ranging between 0 M and 1 M. Thus, binding conditions of pH 8, 0° C., 10 mM NaCl and elution conditions of pH 6, 30° C., and 0.5 M NaCl might be selected for most protein targets. Other pairs of binding and release conditions based on this estimated stability envelope would include: (1) Binding: pH 6, 25° C., 0.5 M NaCl and Elution: pH 8, 0° C., 10 mM NaCl; (2) Binding: pH 7, 0° C., 10 mM NaCl and Elution: pH 7, 35° C., 150 mM NaCl, 4 M urea; and (3) Binding: pH 8.0, 25° C., and 150 mM NaCl and Elution: pH 6, 25° C., and 150 mM NaCl.

If additional information concerning the stability of a particular target in a feed stream must be ascertained to make suitable selections of binding and release conditions, stability over a range of one or more parameters may be determined easily. Illustrative tests to establish a useful stability envelope for a target are described below. Many modifications of such tests are possible that will also yield useful stability data, and such modifications will suggest themselves to those skilled in this art. It is not important to determine the boundaries of stability with high accuracy, rather it is only necessary to define a range of conditions within which the target is stable and within which two distinct conditions (for binding and release) can be selected.

If stability conditions for a particular target are extremely narrow, it should be kept in mind that the target must not denature over the time period necessary to perform the affinity purification: After recovery of the target even under conditions of borderline stability, the product may be returned to a solution where it is highly stable before further processing.

Illustrative Tests to Establish a Stability Envelope for a Target Temperature Stability First, the temperature, $T_m$, at which the target molecule denatures or shows a substantial loss of activity may be measured in a solution at pH 7, 150 mM salt. This $T_m$ could be determined, for example, using a scanning calorimeter. It is to be understood that $T_m$ indicates a fairly sharp transition but that prolonged incubation at slighty lower temperatures (at the upper end of a temperature stability range) could result in loss of activity. Thus, it is preferred that the termperature boundary of the stability envelope be drawn a few degrees inside the limit defined by $T_m$. Alternatively, temperature stability may be determined by measuring the activity of samples of a target after incubation for a time (e.g., from 15 minutes up to 24 hours) at a set of temperatures, such as 25° C., 37° C., 45° C., 55° C., and 65° C. If the target shows no loss of activity a and significant loss of activity at the next temperature, the boundary of the temperature range may be determined to the degree of accuracy desired by measuring activity at one or more intermediate temperatures. Next, it can be determined whether the target disaggregates or precipitates at low temperature, down to the freezing point of 150 mM saline.

pH Stability

The range of pH for which the target retains activity at several temperatures (e.g., 4° C., 25° C., 37° C., and 50° C.) may be determined. This can be done in a scanning calorimeter by measuring $T_m$ for a variety of pH values. Note that $T_m$ defines an upper boundary for stability at a given pH and that the envelope of stability should be drawn a few degrees lower at each pH. For example, one could measure $T_m$ for pH 7, 6, 8, 5, 9, 4, 10, etc. until a boundary is determined. Alternatively, a sample of the target may be incubated for an appropriate time (such as 20 minutes) at a particular temperature (25° C., 37° C., and 50° C.) at pH 2, 3, 4, 5, 6, 7, 8, 9, 10, 11, and 12 and the activity measured after adjusting the pH to one suitable for determination of the activity. If the range is strongly temperature dependent, the range of pH may be determined over which the target retains activity at additional temperatures (e.g., 15° C., 30° C., 43° C., and 60° C.).

Range of Ionic Strength for Which Target is Soluble and Stable

This is advantageously measured at two or three temperatures. For example, useful temperatures might be 4° C. (or the lowest at which the target does not precipitate or disaggregate), 25° C., and 5° C. below $T_m$ (or the highest temperature at which target shows no significant loss of activity). $T_m$ might be measured in a scanning calorimeter for a series of concentrations of NaCl, such as 1 mM, 5 mM, 50 mM, 150 mM ,500 mM, 1 M and 3 M. In each case, an appropriate buffer should be added to maintain the pH at a specific value, for example, pH 7 or pH 8.

Most proteins are soluble in water with some salt. Proteins often precipitate or crystallize at very low salt or at very high salt. Salts used for precipitation of proteins include NaCl, $(NH_4)_2SO_4$, ammonium acetate, KCl, potassium phosphate ($KH_2PO_4$ and $K_2HPO_4$), sodium phosphate ($NaH_2PO_4$ and $Na_2HPO_4$), and the like. Preferably, the points (high salt and low salt) at which solubility of the target drops sharply are determined for two or three salts, such as NaCl, ammonium sulfate, and ammonium acetate.

Stability and Solubility of the Target with Respect to Chaotropes

Urea, guanidinium chloride, sodium thiocyanate, guanidinium thiocyanate, and the like are known to disrupt the interactions of proteins with other molecules. These agents can also cause proteins to unfold. Preferably, the stability of the target is measured with respect to increasing concentrations of one or more of the following: urea, guanidinium chloride, sodium thiocyanate, sodium isothiocyanate, N-methylurea, and the like. Typically, the stability of a protein to denaturation by heat is parallel to its stability against denaturation by urea and other chaotropes.

Whether the Target Requires Specific Ions for Stability

Some proteins bind metal ions (such as $Mg^{++}$, $Zn^{++}$, $Ca^{++}$). In some cases, the proteins denature if the metal ion is removed, for example, by exposure to chelating agents such as EDTA. Whether the target contains metals may be determined by an elemental analysis. If the target does contain metal ions, it may be determined whether exposure to EDTA or dialysis against distilled water causes the target to lose activity.

Stability and Solubility of the Target in Organic Solvents and Organic Solutes

Preferably, the stability and solubility of the target is determined in organic solvents, in mixtures of water and organic solvents, and in water with added organic solutes. For example, the stability and solubility of the target is measured in one or more of the following: acetonitrile (ACN) and water/ACN mixtures, methanol (MeOH) and water/MeOH mixtures, ethanol (EtOH) and water/EtOH mixtures, isopropyl alcohol (IPA) and water/SBA mixtures, dimethylformamide (DMF) and water/DMF mixtures, dimethylsulfoxide (DMSO) and water/DMSO mixtures, secondary butyl alcohol (SBA) and water/SBA mixtures, acetone and water/acetone mixtures, and the like. In addition, the stability and solubility of the target is tested in water with various added amounts of organic solutes such as formamide, N-methylformamide, acetamide, N-methylacetamide, and the like.

Phage Display and Organic Solvents

A preferred method of obtaining selective ligands that bind targets is to select from a library of proteins displayed on phage, such as M13. Thus, if phage display libraries are used, it is of interest to determine whether organic solvents disrupt the phage. ACN, MeOK, and DMSO are particularly preferred because these solvents do not ruinously affect M13 phage. In particular, the following conditions allow substantial survival of M13.

TABLE 1

Stability of M13 in Various Organic Solvents

| Solvent | % solvent by volume, in Luria broth | Survival after 20 min. (%) | Survival after 60 min. (%) |
|---|---|---|---|
| ACN | 10 | 84 | 74 |
|  | 20 | 80 | 91 |
|  | 40 | 92 | 89 |
|  | 80 | 30, 37 | 8, 3 |
| DMSO | 2 | 84 | 89 |
|  | 5 | 68 | 86 |
|  | 10 | 96 | 86 |
|  | 20 | 73 | 82 |
|  | 80 | 1 | >1 |
| MeOH | 10 | 110 | 80 |
|  | 20 | 93 | 84 |

TABLE 1-continued

Stability of M13 in Various Organic Solvents

| Solvent | % solvent by volume, in Luria broth | Survival after 20 min. (%) | Survival after 60 min. (%) |
|---|---|---|---|
| | 40 | 92 | 84 |
| | 80 | 80, 21 | 70, 6 |

Incubation for 20 minutes with 80% EtOH, IPA, or DMF left no surviving phage. These solvents may be used with phage at lower concentrations.

Knowledge of the target may suggest other manipulable solution conditions that could be useful. For example, the stability of a sugar binding protein may be influenced by the concentration Isolation of Affinity ligands Selecting Binding and Release Conditions Using a proposed or an empirically determined envelope of stability for the target molecule, two solution conditions are selected, i.e. binding conditions and release conditions. The binding conditions are a set of solution conditions under which it is desired that a discovered affinity ligand will bind the target; the release conditions are a set of solutions conditions under which it is desired that a discovered affinity ligand will not bind the target. The two conditions may be selected to satisfy any criterion of the practitioner, such as ease of attaining the conditions, compatability with other purification steps, lowered cost of switching between conditions compared to other affinity media, etc. Preferably the two solution conditions are (a) well within the boundaries of the stability envelope for the target and (b) far apart with respect to at least one solution parameter. For example, if the target is stable over a wide pH range, then favorable binding conditions might be pH 11, 150 mM salt, 25° C. and favorable release conditions might be pH 3, 150 mM salt, 25° C. For a different target having a narrow range of pH stability (for example, pH 6.2 to 7.8) but being stable over a wide range of salinity, two useful conditions might be binding conditions: pH 7.2, 3 M NaCl, 25° C. and release conditions: pH 7.2, 2 mM NaCl, 25° C. A third target might have a narrow range of pH stability but a wide range of stability versus acetonitrile. For this third hypothetical target, useful conditions might include binding conditions: pH 7.0, 100 mM NaCl, 100 mM $K_2HPO_4$, 25° C. and release conditions: pH 7.0, 5 nM NaCl, 50% (v/v) acetonitrile.

Selection of a Candidate Binding Domain

In conjunction with selecting specific solution conditions for the desired binding and release of the target, a candidate binding domain must be selected to serve as a structural template for the engineered affinity ligands that will exhibit the desired binding and release capabillities. The binding domain may be a naturally occurring or synthetic protein, or a region or domain of a protein. The candidate binding domain may be selected based on knowledge of a known interaction between the candidate binding domain and the target, but this is not critical. In fact, it is not essential that the candidate binding domain have any affinity for the target: Its purpose is to provide a structure from which a multiplicity (library) of analogues can be generated, which multiplicity of analogues will include one or more analogues that exhibit the desired binding and release properties (and any other properties selected for). Thus, the binding conditions and the release conditions discussed infra may be selected with knowledge of the exact polypeptide that will serve as the candidate binding domain, or with knowledge of a class of proteins or domains to which the candidate binding domain belongs, or completely independently of the choice of the candidate binding domain. Similarly, the binding and/or release conditions may be selected with regard to known interactions between a binding domain and the target, e.g., to favor the interaction under one or both of the solution conditions, or they may be selected without regard to such known interactions. Likewise, the candidate binding domain can be selected taking into account the binding and/or release conditions or not, although it must be recognized that if the binding domain analogues are unstable under the binding or release conditions no useful affinity ligands will be obtained.

In selecting a candidate binding domain, the object is to provide a template or parental structure from which a library of similarly structured analogue domains can be generated. The analogue library will preferably be a biased library (as opposed to a randomly generated library), in that variegation of the basic domain to create the library will be carried out in such a way as to favor the properties desired for the affinity ligands.

The nature of the candidate binding domain greatly influences the properties of the derived proteins (analogues) that will be tested against the target molecule. In selecting the candidate binding domain, the most important consideration is how the analogue domains will be presented to the target, i.e., in what conformation the target and the analogues will come into contact. In preferred embodiments, for example, the analogues will be generated by insertion of synthetic DNA encoding the analogue into a replicable genetic package, resulting in display of the domain on the surface of a microorganism such as M13 phage, using techniques as described, e.g., in U.S. Pat. No. 5,403,484 (Ladner et al.) and U.S. Pat. No. 5,223,409 (Ladner et al.), incorporated herein by reference.

Structured potypeptides offer many advantages as candidate binding domains over unstructured peptides. Mutation of surface residues in a protein will usually have little effect on the overall structure or general properties (such as size, stability, temperature of denaturation) of the protein; while at the same time mutation of surface residues may profoundly affect the binding properties of the protein. This has been fully documented, for example, for BPTI-homologous Kunitz domains (see Ladner, 1995). Mutating surface residues on proteins or structured domains can lead to greater diversity of properties for the analogues than is obtained by mutating unstructured peptides because the protein framework or the structure of the domain holds the mutated residues in conformations that differ from residue to residue and from framework to framework. This is especially important for hydrophobic side groups that would become buried unless constrained in a structure. The more tightly a peptide segment (domain) is constrained, the less likely it is to bind to any particular target. If it does bind, however, the binding is likely to be tighter and more specific. Thus, it is preferred to select a candidate binding domain and, in turn, a structure for the peptide analogues, that is constrained within a framework having some degree of rigidity. Alternatively, more than one candidate binding domain structure can be selected, in order to increase the size of the library of analogues and to introduce additional variegated structures for presentation to the target. As the size of the library is increased, and higher numbers and diversely structured analogues are prepared, the probability of including a useful framework and displayed functional groups increases to the point where high-affinity ligands can be found for almost any target.

The size of the candidate binding domain is also an important consideration. Small proteins or polypeptides offer several advantages over large proteins, such as monoclonal antibodies (see Ladner, 1995). First, the mass per binding site is reduced. Highly-stable protein domains having low molecular weights, e.g., Kunitz domains (~7 kDa), Kazal domains (~7 kDa), Cucurbida maxima trypsin inhibitor (CMTI) domains (~3.5 kDa), and endothelin (~2 kDa), can show much higher binding per gram thin do antibodies (~150 kDa) or single-chain antibodies (~30 kDa).

Second, the possibility of non-specific binding is reduced because there is less surface available.

Third, small proteins or polypeptides can be engineered to have unique tethering sites in a way that is impracticable for antibodies. For example, small proteins can be engineered to have lysines only at sites suitable for tethering (e.g., to a chromatography matrix), but this is not feasible for antibodies. It is often found that only a small fraction of immobilized antibodies are active, possibly due to inappropriate linkage to the support.

Most small proteins or polypeptides that are stabilized by disulfides do not contain cysteines that are not involved in disulfides. This is because the oxidizing conditions that cause disulfide formation for stabilizing the protein also lead to disulfide formation by otherwise unpaired cysteines. Thus, small proteins having stabilizing disulfides and an odd number of cysteines tend to form disulfide linked dimers (e.g., homodimers or heterodimers). The disulfides between domains are more easily reduced than are the stabilizing intradomain disulfides. Thus, by selective reduction it is possible to obtain monomeric disulfide-stabilized domains having a single free thiol. Such thiols can be used for highly stable immobilization of these domains by formation of a thioether with iodoacetamide, iodoacetic acid, or similar α-iodo carboxylic acid groups.

Small protein or polypeptide domains also can be chemically synthesized, which permits special immobilizing groups to be incorporated in a way that does not interfere with binding to the target. For instance, if small disulfide-containing proteins are chemically synthesized, the amino acid sequence can be altered by adding an extra cysteine residue with the thiol blocked in a different manner from other cysteines elsewhere in the sequence. The selected thiols can be deblocked and disulfides allowed to form, then the added cysteine can be deblocked and the molecule can be immobilized by reaction with a suitable material such as a substrate containing immobilized $NH_2$—CO—$CH_2I$.

Fourth, a constrained polypeptide structure is more likely to retain its functionality when transferred with the structural domain intact from one framework to another. For instance, the binding domain structure is likely to be transferable from the framework used for presentation in a library (e.g., displayed on a phage) to an isolated protein removed from the presentation framework or immobilized on a chromatographic substrate.

There are many small, stable protein domains suitable for use as candidate binding domains and for which the following useful information is available: (1) amino acid sequence, (2) sequences of several homologous domains, (3) 3-dimensional structure, and (4) stability data over a range of pH, temperature, salinity, organic solvent, oxidant concentration. Some examples are: Kunitz domains (58 amino acides, 3 disulfide bonds), Cucurbida maxima trypsin inhibitor domains (31 amino acids, 3 disulfide bonds), domains related to guanylin (14 amino acids, 2 disulfide bonds), domains related to heat-stable enterotoxin IA from gram negative bacteria (18 amino acids, 3 disulfide bonds), EGF domains (50 amino acids, 3 disulfide bonds), kringle domains (60 amino acids, 3 disulfide bonds), fugal carbohydrate-binding domains (35 amino acids, 2 disulfide bonds), endothelin domains (18 amino acids, 2 disulfide bonds), and Streptococcal G IgG-binding domain (35 amino acids, no disulfide bonds). Most, but not all of these contain disulfide bonds that rigidify and stabilize the structure. Libraries based on each of these domains, preferably displayed on phage or other genetic packages, can be readily constructed and used for the selection of binding analogues.
Providing a Library of Candidate Binding Domain Analogues Once a candidate binding domain has been selected, a library of potential affinity ligands is created for screening against the target at the binding and elution (release) conditions. The library is created by making a series of analogues, each analogue corresponding to the candidate binding domain except having one or more amino acid substitutions in the sequence of the domain. The amino acid substitutions are expected to alter the binding properties of the domain without significantly altering its structure, at least for most substitutions. It is preferred that the amino acid positions that are selected for variation (variable amino acid positions) will be surface amino acid positions, that is, positions in the amino acid sequence of the domains which, when the domain is in its most stable conformation, appear on the outer surface of the domain (i.e., the surface exposed to solution). Most preferably the amino acid positions to be varied will be adjacent or close together, so as to maximize the effect of substitutions. In addition, extra amino acids can be added into the structure of the candidate binding domain. In preferred embodiments, especially where a great deal of information is available concerning the 3-dimensional structure of the target or interactions of the target with other molecules, particularly the candidate binding domain, those amino acid positions that are essential to binding interactions will be determined and conserved in the process of building the analogue library (i.e., the amino acids essential for binding will not be varied).

The object of creating the analogue library is to provide a great number of potential affinity ligands for reaction with the target molecule, and in general the greater the number of analogues in the library, the greater the likelihood that a member of the library will bind to the target and release under the preselected conditions desired for release. On the other hand, random substitution at only six positions in an amino acid sequence provides over 60 million analogues, which is a library size that begins to present practical limitations even when utilizing screening techniques as powerful as phage display. It is therefore preferred to create a biased library, in which the amino acid positions designated for variation are considered so as to maximize the effect of substitution on the binding characteristics of the analogue, and the amino acid residues allowed or planned for use in substitutions are limited to those that are likely to cause the analogue to be responsive to the change in solution conditions from the binding conditions to the release conditions.

As indicated previously, the techniques discussed in U.S. Pat. No. 5,223,409 are particularly useful in preparing a library of analogues corresponding to a selected candidate binding domain, which analogues will be presented in a form suitable for large-scale screening of large numbers of analogues with respect to a target molecule. The use of replicable genetic packages, and most preferably phage display, is a powerful method of generating novel polypeptide binding entities that involves introducing a novel DNA segment into the genome of a bacteriophage (or other amplifiable genetic package) so that the polypeptide encoded by the novel DNA appears on the surface of the phage. When the novel DNA contains sequence diversity, then each recipient phage displays one variant of the initial (or "parental") amino acid sequence encoded by the DNA, and the phage population (library) displays a vast number of different but related amino acid sequences.

A phage library is contacted with and allowed to bind the target molecule, and non-binders are separated from binders. In various ways, the bound phage are liberated from the target and amplified. Since the phage can be amplified through infection of bacterial cells, even a few binding phage are sufficient to reveal the gene sequence that encodes a binding entity. Using these techniques it is possible to recover a binding phage that is about 1 in 20 million in the population. One or more libraries, displaying 10–20 million or more potential binding polypeptides each, can be rapidly screened to find high-affinity ligands. When the selection process works, the diversity of the population falls with each round until only good binders remain, i.e., the process converges. Typically, a phage display library will contain several closely related binders (10 to 50 binders out of 10 million). Indications of convergence include increased binding (measured by phage titers) and recovery of closely related sequences. After a first set of binding polypeptides is identified, the sequence information can be used to design other libraries biased for members having additional desired properties, e.g., discrimination between two highly similar molecules.

Such techniques make it possible not only to screen a large number of analogues but make it practical to repeat the binding/elution cycles and to build secondary, biased libraries for screening analog-displaying packages that meet initial criteria. Thus, it is most preferred in the practice of the present invention (1) that a library of binding domain analogues is made so as to be displayed on replicable genetic packages, such as phage; (2) that the library is screened for genetic packages binding to the target molecule wherein the binding conditions of the screening procedure are the same as the binding conditions preselected for the desired affinity ligand; (3) that genetic packages are obtained by elution under the release conditions preselected for the affinity ligand and are propagated; (4) that additional genetic packages are obtained by elution under highly disruptive conditions (such as, e.g., pH 2 or lower, 8 M urea, or saturated guanidinium thiocyanate, to overcome extremely high affinity associations between some displayed binding domain analogues and the target) and are propagated; (5) that the propagated genetic packages obtained in (3) or (4) are separately or in combination cycled through steps (2) and (3) or (4) for one or more (e.g., one to five) additional cycles; and (6) a consensus sequence of high-affinity binders is determined for analogues expressed in genetic packages recovered from such cycles; (7) that an additional biased library is constructed based on the original framework (candidate binding domain) and allowing the high-affinity consensus at each variable amino acid position, and in addition allowing other amino acid types selected to include amino acids believed to be particularly sensitive to the change between the binding conditions and the release conditions; (8) that this biased library is screened for members that (a) bind tightly (i.e., with high affinity) under the binding conditions and (b) release cleanly (i.e., readily dissociate from the target) under the release conditions.

Use of the Affinity ligands in Chromatography

After members of one or more libraries are isolated that bind to a target with desired affinity under binding conditions and release from the target as desired under release conditions, isolation of the affinity ligands can be accomplished in known ways. If, for example, the analogue library is composed of prospective affinity ligands expressed on phage, released phage can be recovered, propagated, the synthetic DNA insert encoding the analogue isolated and amplified, the DNA sequence analyzed and any desired quantity of the ligand prepared, e.g., by direct synthesis of the polypeptide or recombinant expression of the isolated DNA or an equivalent coding sequence.

Additional desired properties for the ligand can be engineered into an analogue ligand in the same way release properties were engineered into the ligand, by following similar steps as described herein.

The affinity ligands thus isolated will be extremely useful for isolation of the target molecule by affinity chromatography methods. Any conventional method of chromatography may be employed. Preferably, an affinity ligand of the invention will be immobilized on a solid support suitable, e.g., for packing a chromatography column. The immobilized affinity ligand can then be loaded or contacted with a feed stream under conditions favorable to formation of ligand/target complexes, non-binding materials can be washed away, then the target can be eluted under conditions favoring release of the target molecule from a ligand/target complex. Alternatively, bulk chromatography can be carried out by adding a feed stream and an appropriately tagged affinity ligand together in a reaction vessel, then isolating complexes of the target and ligand by making use of the tag (e.g., a polyHis affinity tag, which can by used to bind the ligand after complexes have formed), and finally releasing the target from the complex after unbound materials have been eliminated.

It should be noted that although precise binding and release properties are engineered into the affinity ligands, subsequent use in affinity purification may reveal more optimal binding and release conditions under which the same isolated affinity ligand will operate. Thus, it is not critical that the affinity ligand, after isolation according to this invention, be always employed only at the binding and release conditions that led to its separation from the library.

Affinity Constants

Assume that an affinity ligand is isolated having a molecular weight of approximately 3,000 Daltons (~3 kDa)(Cf., e.g., CMTI derivatives infra). Also assume that the ligand can be loaded onto a suitable chromatographic support at an effective concentration of 3 mM (i.e., ~10 g/L).

Assume a target with molecular weight of 50 kDa and produced at 10 mg/L from cell culture medium. The concentration of protein is $(0.01 \text{ g/L}) \div (5 \times 10^4 \text{ g/mole}) = 0.2 \ \mu\text{M}$. If the ligand is present at 3 mM, then 1 L of affinity material could capture 3 millimoles (167 g) of target.

Assume that the ligand binds the target according to the simple mass-action equation (1):

$$\frac{K_D}{[ligand]} = \frac{[target]}{[complex]} \equiv \frac{1}{X} \quad \quad \quad (1)$$

The fraction of target that can be captured is given in equation (2):

$$Fraction\text{-}of\text{-}Target\text{-}Bound = \frac{1}{1+(1/X)} \quad \quad \quad (2)$$

Thus, the Fraction-of-Target-Bound can be controlled by the dissociation constant $K_D$ and the amount of ligand loaded on the support. $K_D$ is a function of the solution conditions but is inherent in the affinity ligand molecule. The value of $K_D$ under Binding Conditions is $K_D^{BC}$ and the value of $K_D$ under Elution Conditions is $K_D^{EC}$.

| | Fraction of Binding (in one equilibrium stage) | |
|---|---|---|
| X = [ligand]/$K_D$ | Fraction-of-Target-Bound $(1 + (1/X))^{-1}$ | $K_D$ (Assumed [ligand] = 3 mM) |
| 0.001 | 0.001 | 3 M |
| 0.010 | 0.0099 | 300 mM |
| 0.020 | 0.0196 | 150 mM |
| 0.040 | 0.0385 | 75 mM |
| 0.100 | 0.0909 | 30 mM |
| 0.500 | 0.03333 | 6 mM |
| 1.000 | 0.50 | 3 mM |
| 2.000 | 0.667 | 1.5 mM |
| 5.000 | 0.8333 | 600 μM |
| 10.000 | 0.90909 | 300 μM |
| 100.000 | 0.990099 | 30 μM |
| 1000.000 | 0.999000999 | 3 μM |
| 10000.000 | 0.999900009999 | 300 nM |

The foregoing table shows how the Fraction-of-Target-Bound is expected to vary with the ratio [ligand]/$K_D$. Acceptable capture is assumed to be greater Man 0.9, but the invention is not limited to any particular capture level. If [ligand] is approximately 3 mM then acceptable capture can be obtained with $K_D^{BC}$ at 300 μM or lower. More effective capture is obtained with [ligand]/$K_D^{BC} \geq 100$, and these higher values are preferred. The higher the value of [ligand]/$K_D^{BC}$ the better with the proviso that [ligand]/$K_D^{EC}$ must be small enough to allow recovery of the target. If more affinity ligand than 3 mM can be loaded on a support, then ligands having higher values of $K_D$ can be used.

Acceptable elution involves [ligand]/$K_D^{EC}$<10; lower values of [ligand]/$K_D^{EC}$ are preferred. In particular, [ligand]/$K_D^{EC}$<0.1 is preferred and [ligand]/$K_D^{EC}$<0.01 is more preferred. The lower [ligand]/$K_D^{EC}$ is the better without limit. After the ratio [ligand]/$K_D^{EC}$ is below 0.001, there is little to be gained in equilibrium release, but ligands having very high $K_D$ may have higher off rates and so may be superior in practice by releasing target very rapidly.

Thus, to have efficient capture and elution, theory indicates that $(K_D^{EC}/K_D^{BC})$ should be 1000 or greater; the higher this ratio, the better. The process is satisfactory if $(K_D^{EC}/K_D^{BC})>10$ if at least 10% of bound material can be liberated under elution conditions. Nevertheless, the invention is not limited to any particular value of $(K_D^{EC}/K_D^{BC})$. ligands having very high affinity for a target could give higher specificity, especially if the affinity material is loaded with a slight excess of target so that impurities having less affinity are crowded out in favor of target. For very high-affinity ligands, the amount of excess needed to crowd out impurities is small.

$K_D^{EC}$ is as important as $K_D^{BC}$. Preferably, $K_D^{EC}$ is no greater than 0.1 and more preferably no greater than 0.01. Nevertheless, affinity purification is functional even if $K_D^{EC}=1$, which theoretically allows release of 50% of the bound material: Four equilibrium washes would lead to 94% recovery of the material captured under the binding conditions (i.e., 50%+25%+12.5%+6.25%).

Hypothetically, 1 L of an immobilized ligand having $K_D^{BC}=1$ μM and attached to a support at 3 mM could capture 99% of a target from about 15,000 L of a 0.2 μM solution (10 mg/L of a 50 kDa target molecule).

It will be understood that the affinity ligand attached to a suitable support may be used in many different ways to capture the target, including chromatographic embodiments with many equilibrium stages. For example, the ligand-support may be loaded into columns and the solution containing the target caused to flow through the column and (optionally) recirculated until substantially all of the target is bound or the ligand support is saturated with target. Alternatively, the ligand-support may be mixed (shaken or stirred) with the target-containing solution until binding is complete.

If $K_D^{EC}$ is 3 mM and the loading is 3mM, then four 1 L equilibrated washes could recover up to 2.82 millimoles (94% of 3 mM) in 4 L to give a 670 μM solution of target, i.e., a 3350-fold concentration of the target as compared to the feed stream. Furthermore, it is expected that most impurities would be removed.

If $K_D^{EC}$ is 30 mM and the loading is 3 mM, then two 1 μL equilibrated washes could recover up to 2.98 millimoles (99% of 3 mM) in 2 L to give a 1.49 mM solution of target, i.e., a 7450-fold concentration of the target as compared to the feed stream. If, on the other hand, $K_D^{EC}$ is 0.3 mM and the loading is 3 mM, then twenty-four 1 L equilibrated washes could recover up to 2.70 millimoles (90% of 3 mM) in 24 L to give a 112 μM solution of target, i.e., a 560-fold concentration of the target as compared to the feed stream, but this would not be very desirable. Thus, a practical limit for ligand on a support is [ligand]/$K_D^{EC}=10$ with lower values being preferred.

The level of loading of support with ligand governs three factors: (a) the fraction of target that can be captured from a feed stream, (b) the absolute amount of target that can be captured, and (c) the amount of impurities that will be captured. Theoretical behavior of the first two factors have been given. Since the impurities in a feed stream are likely to be complex and idiosyncratic, the interactions between [ligand] and the binding and elution of impurities is best worked out empirically.

Given a particular affinity ligand, an appropriate loading for optimal separation can be calculated. Assuming an affinity ligand that has $K_D^{BC}$ of 3 mM and $K_D^{EC}$ of 3 μM, if loaded onto a support at 3 mM, capture of target would be complete. However, under elution conditions only>1% could be eluted. If the ligand were loaded at 3 μM, target could be captured and released with X=1. Alternatively, variants of the selected affinity ligand could be prepared in which amino acids in or near the binding region would be changed so that one or more having a more suitable (i.e., lower) affinity would be obtained.

The foregoing discussion has been in terms of batch binding and elution. An alternative approach is isocratic chromatorgraphy with many equilibrium stages. Affinity ligands that have high on and off rates may be more effective in chromatographic processes. For chromatographic procedures, the most important attributes of the ligand are moderate affinity (1 μM to 1 mM) for the target and much less affinity for any other component of the feed stream.

To increase the likelihood of recovering binding analogues having lower affinities, the removal of unbound analogues (see step (g), above), e.g., by washing, may be very brief, especially in the early rounds of screening. For instance, a binding domain having a $K_D=3$ μM could have a $K_{on}=10^3$/molar/sec. and $K_{off}=10^3$/sec. This corresponds to $\tau_{1/2}=694$ sec.≈12 min. If the library originally contains $10^7$ different analogues, then a sample of $10^{11}$ analogues will have 10,000 of each member of the library. If 5,000 of a particular analogue bind to the target, and washes of three half times ($\tau_{1/2}$) are employed (~35 min.), then 625 analogues would be captured. Even though curtailed washing may give a higher background of non-specific analogues, it may be preferred to ensure that fast-on/fast-off members of the library are retained into the next rounds.

From the foregoing, it can be seen that the highest affinity ligand is not necessarily the best for controllable or cost effective recovery of a target molecule. The method of the invention permits selection of ligands that have a variety of desirable characteristics important to the practitioner seeking isolation of a particular target, such as specific binding of the target, coupled with predictable and controlled, clean release of the target, useful loading capacity, acceptably complete elution, re-usability/recyclability, etc.

Elimination of Closely Related Purities

The present invention also allows selection of affinity ligands that can discriminate between a target molecule and other molecules that are quite similar. Here, the "target" is the molecule to which the affinity ligand should bind and the "specific impurity" is the molecule to which binding is desired to be minimized.

Using the method of the invention, an affinity ligand can be found that is able to distinguish between a protein that contains Asn residues but not the deamidated derivative in which Asn has been chemically converted to Asp. Similarly, affinity ligands can be found that are useful to separate the R form of an isomeric organic compound from the S form.

There are at least three ways to achieve this kind of specificity: First, a number of affinity ligands that bind the target could be obtained and tested as clonal isolates for binding to the specific impurity. Second, the specific impurity could be immobolized and those members of a library that have high affinity for the specific impurity could be removed. This "depleted library" could then be screened for binders to the target. Third, while screening a library of potential affinity ligands for binding to the immobilized target, one could include the specific impurity (or specific impurities) in the binding buffer at a sufficient concentration that any member of the library having affinity for both the target and the specific impurity is much more likely to bind the specific impurity than the immobilized target. In this manner the members binding to the target are "engineered" to exhibit a lack of affinity for the specific impurity. The third method is preferred.

For all three methods, it is important that the specific impurity be substantially free of the target. It is preferred that the concentration of target in specific impurity be as low as possible.

In the third method, the specific impurity would be added at a concentration such that the concentration of target free in solution would not be expected to bind a significant portion of any target-binding component of the library. Thus, as the library is screened through several rounds of binding/ washing/elution/amplification, the concentration of specific impurity may be increased, since the concentration of each remaining member of the library increases while the number of members decreases. As long as any target contained in the preparation including the specific impurity cannot tie up all of a potentially useful affinity ligand, then some of the useful affinity ligand will be captured by the immobilized target and will be carried forward to the next round. The following calculation would suggest an appropriate amount of specific impurity to use, but the invention is not limited to the use of any particular level of specific impurity or to any particular theory of binding and competition.

In a phage display library of complexity $10^6$ (i.e., $10^6$ different potential affinity ligand peptides displayed), suppose the titer of the library is $10^{13}$ phage/mL, i.e., $10^7$ phage of each type/mL. If the target is present at effectively 50 $\mu$M and the specific impurity at 0.5% of target, then specific impurity would be added up to 1,000 $\mu$M and have free target be at 5 $\mu$M, which is unlikely to completely inhibit capture of affinity ligands that can bind target in the presence of the specific impurity.

When a library is screened without amplification between rounds, it may be sufficient to add the specific impurity in one of the binding steps. It should be experimentally determined whether early binding steps or late binding steps are the optimal stage at which the specific impurity is to be added.

Isolation of affinity ligands in accordance with this invention will be further illustrated below. The specific parameters included in the following examples are intended to illustrate the practice of the invention, and they are not presented to in any way limit the scope of the invention.

EXAMPLES 1–15

It is often found that proteins that bind to other proteins have one or more hydrophobic side groups that are exposed in the free protein and that become buried when the complex forms. The amino acids Phe, Tyr, Leu, Ile, Val, Met, Trp, Cys, and His have hydrophobic side groups. Phe, Leu, Ile, Val, Met, and Cys (when part of a disulfide) are always hydrophobic. Tyr and Cys (when not part of a disulfide) can be ionized at high pH. His can become ionized at neutral or acidic pH. Proteins that are likely to have exposed hydrophobic regions include protein hormones, receptors for protein hormones, receptors, binding molecules, antibodies, and the like. Enzymes and highly abundant storage and transport proteins (such as trypsin, myoglobin, and hemoglobin) may not have any large hydrophobic regions on the surface.

If a target is known to have exposed hydrophobic regions or is likely to have exposed hydrophobic regions, then a preferred approach is to select for a ligand that binds at high salt (which favors hydrophobic interactions) and 37° C. and that releases at 4° C. (which disfavors hydrophobic interactions) and/or in acetonitrile (which disfavors hydrophobic interactions) at 50% (v/v) and 10 mM NaCl (low salt).

If a target protein has a high number of ionic groups (Asp, Glu, Lys, Arg, and His, as can be determined from the amino acid composition or amino acid sequence), then a preferred approach is to select for a ligand that binds at one pH and releases at a second pH. For example, for a target that is stable between pH 3.0 and pH 9.5, it is advantageous to select for ligands that bind at pH 8.5, 20 mM NaCl, and 10° C., and that release at pH 4.0, 1 M NaCl, and 30° C. Low temperature and low salt favor ionic interactions, while higher salt and temperature reduce the binding force of ionic groups. Alternatively, one could select for ligands that bind at pH 8.5, 1 M NaCl, and 30° C. and that release at pH 4.0, 10 mM NaCl, 10° C., and 10% (v/v) MeOH.

If a water-soluble target has a very low number of ionic groups (Asp, Glu, Lys, Arg, and His for proteins), then it is likely to have many neutral polar groups on the surface (viz., Ser, Thr, Asn, Gln, and Tyr for proteins). Many sugars will fall into this class. Such neutral polar groups (hydroxyl, amide, ether, ester, and the like) are capable of forming hydrogen bonds. Thus, a library having hydrogen bond-forming amino acid types allowed at many positions is likely to contain members that will bind specifically to molecules of this class with useful affinity. Amino acids having side groups that can form hydrogen bonds include Asp (D), Glu (E), His (H), Lys (K), Asn (N), Gln (Q), Arg (R), Ser (S), Thr (T), Trp (W), and Tyr (Y). Hydrogen bonding is strongly affected by PH, ionic strength, dielectric constant of the solvent, and by chaotropes such as urea and guanidinium ions. Hydrogen bonds lose strength at higher temperature. Thus, appropriate binding conditions would have low salt and low dielectric constant, while elution conditions would have high salt, high dielectric constant, and a pH different for the pH of the binding condition, preferably by at least 1 pH unit. For example, binding conditions could be pH 8, 10 mM NaCl, and 4° C., while elution conditions could be pH 6, 500 mM NaCl, and 35° C. Alternatively, one could select for ligands that bind at pH 8.5, 1 M NaCl, and 30° C. and that release at pH 4.0, 10 mM NaCl, 10° C., and 10% (v/v) MeOH.

The solution condition most easily and economically altered is pH. It is well known that a change in the ionization of an amino acid within an intermolecular interface can greatly disrupt the binding of the molecules. Thus, to increase the likelihood that the binding of an analogue to the target will be highly sensitive to changes inpHk the library can be designed to allow a t least His and preferably Glu, Asp, Tyr and Lys at most or all varied positions. It is to be understood that other amino acid types may also be allowed. For example, a library in which each varied position allows the set {His, Asp, Glu, Tyr, Lys, Ala, Ser, Asn, Leu and Phe} would be highly likely to contain ligands that bind to a target in a highly pH-sensitive manner. Libraries that allow only the set {His, Glu, Asp and Tyr} are also likely to function, but allowing additional amino acid types increases the likelihood of obtaining binding under the first solution condition. One or two groups that change ionization state within the interface is sufficient to disrupt the binding under the second set of solvent conditions. As shown in Table 2, the $pK_a$s of His, Glu, Asp, Tyr and Lys are in the range 3.5 to 11, a range of pH over which many proteins are stable. In proteins, however, the positioning of each side group can influence its actual $pK_a$. For example, a Lys held in close proximity to an Arg can show a lower $PK_a$ than it otherwise would.

Using the type of information in Tables 2 and 3 relating to the reactivity of amino acid side chains and the properties amino acid groups are likely to confer on a protein in solution, it is possible to select the amino acid substitutions necessary for the design of libraries that will have increased likelihood of containing candidate binding domains that are sensitive to the particular kinds of changes in solvent conditions (moving from binding to elution conditions) where it is desired that the affinity separation process will operate.

TABLE 2

Ionizable Groups of Proteins

| Group | Amino Acid Type | $pK_a$ range |
|---|---|---|
| α-Amino | any except Pro | 6.8–8.0 |
| α-Carboxyl | any | 3.5–4.3 |
| β-Carboxyl | Asp | 3.9–4.0 |
| γ-Carboxyl | Glu | 4.3–4.5 |
| δ-Guanido | Arg | 12.0 |
| ε-Amino | Lys | 10.4–11.1 |
| Imidazole | His | 6.0–7.0 |
| Thiol | Cys (not in disulfide) | 9.0–9.5 |
| Phenolic hydroxyl | Tyr | 10.0–10.3 |

(From Creighton, Proteins: Structures and Molecular Properties, 2nd Ed. (W. H. Freeman and Co., New York, 1993), p. 6.)

Table 3 gives classes of amino acid types that are likely confer on a protein binding that is sensitive to the listed change in solvent conditions. Preferred candidate binding domain analogues of the present invention contain disulfide bonds that stabilize the structure and thus allow the domains to exhibit high affinity, specificity, and stability.

TABLE 3

Classes of amino acids expected to confer sensitivity to particular solvent conditions on proteins having these amino acids in a binding interface.

| Solution Condition to be altered | Example | Amino Acid Types | Sample Conditions Bind | Release |
|---|---|---|---|---|
| pH | 1 | His (most preferred) | pH > 7<br>high salt<br>high temp. | pH < 6<br>low salt<br>low temp. |
|  | 2 | His (most preferred) | pH 8.0<br>500 mM NaCl<br>33° C. | pH 5.75<br>10 mM NaCl<br>4° C. |
|  | 3 | Asp, Glu, Lys, Arg, Tyr, Cys (not in disulfide) (preferred) | any pH<br>low temp. | a different pH<br>high temp. |
|  | 4 | Asp, Glu, Lys, Arg, Tyr, Cys (not in disulfide) (preferred) | pH 3.5<br>4° C.<br>50 mM NaCl | pH 7.5<br>30° C.<br>50 mM NaCl |
|  | 5 | His, Asp, Glu, Lys, Arg, Tyr, Cys (not in disulfide), Asn, Gln, Asn, Ser, Thr | any pH<br>low salt | a different pH<br>high salt |
|  | 6 | His, Asp, Glu, Lys, Arg, Tyr, Cys (not in disulfide), Asn, Gln, Asn, Ser, Thr | pH 8.2<br>10 mM NaCl<br>25° C. | pH 5.71<br>1M NaCl<br>25° C. |
| Salt | 7 | Asp, Glu, Lys, Arg, His, Asn, Gln, Ser, Thr, Tyr, Cys (not in disulfide) | low salt | high salt |
|  | 8 | Asp, Glu, Lys, Arg, His, Asn, Gln, Ser, Thr, Tyr | 5 mM KCl<br>25° C. | saturated KCl<br>25° C. |
|  | 9 | Asp, Glu, Lys, Arg, His, Asn, Gln, Ser, Thr, Tyr, and {Leu, Ile, Met, Phe, Tyr, Trp, Val} | 3M KCl | 5 mM KCl |

TABLE 3-continued

Classes of amino acids expected to confer sensitivity to particular solvent conditions on proteins having these amino acids in a binding interface.

| Solution Condition to be altered | Example | Amino Acid Types | Sample Conditions Bind | Release |
|---|---|---|---|---|
| Organic Solvent | 10 | Leu, Ile, Val, Phe, Tyr, Trp, Met, Ala | water 1M NaCl 25° C. | water:ACN, (50/50 v/v) no salt |
|  | 11 | Leu, Ile, Val, Phe, Tyr, Trp, Met, Ala, Ser, Thr, Asn, Gln | water 1M NaCl 25° C. | 30% MeOH 20 mM $NH_4$ acetate |
| Temperature | 12 | Leu, Ile, Val, Phe, Tyr, Trp, Met, Ala | 33° C. pH 7 1M KCl | 0° C. pH 7 10 mM KCl |
| Chaotropes and axillary solutes | 13 | Gln, Ser, Thr, Asn, Tyr, His (Asp, Glu, Lys, and Arg also) | 10° C. pH 7 10 mM NaCl | 25° C. pH 7 100 mM NaCl 3M urea |
|  | 14 | Asp, Glu | 2° C. pH 7 10 mM $CaCl_2$, 50 mM NaCl | 25° C. pH 7 25 mM EDTA 25 mM NaCl |
|  | 15 | Arg, Lys | 4° C. 100 mM $PO_4$ pH 7.5 | 20° C. pH 7.5 10 mM KCl |

Example 1 illustrates proposed binding and release conditions for a library of binding domain analogues in which histidine is allowed at many or all variable positions. At pH>7, His is uncharged and the side group is hydrophobic, although it can donate and receive hydrogen bonds. High salt and high temperature reduce the contribution to binding energy of ionic interactions. Thus, binding at high salt and high temperature decreases the chance of obtaining a binder having strong ionic interactions and increases the chance of obtaining a ligand that has hydrophobic interactions. The release conditions of low salt and low temperature increase the importance of ionic interactions, particularly the effect of incorrect ionic interactions. Thus, a complex that has one or more His residues in the binding interface is likely to be destabilized at acidic pH and low salt.

Example 2 illustrates selection from a library having His allowed at many or all variable positions. The binding and release conditions are selected to foster isolation of one or more binding domains that bind the target in a manner that is strong at pH 8.0 but is very sensitive to lowering the pH.

Histidine is not the only amino acid that can form pH-sensitive interactions. The amino acids shown in Example 3 are all capable of being ionized in the pH range in which many proteins are stable. Often, the pH at which ionization takes place is highly context-dependent. Thus, an aspartic acid side group within a protein-target interface may not have a $PK_a$ within the range shown in Table 2. When a group within a protein-target interface changes ionization state, it is quite likely that the stability of the complex will be strongly altered. Thus, if a complex is stable at one pH, it is unlikely to be stable at a pH sufficiently different that a group within the interface has changed ionization state. The pH at which such a transition takes place is difficult to calculate and need not be one of the $pK_a$s shown in Table 2.

Example 4 illustrates that a library of analogues having many Asp, Glu, Lys, Arg, Tyr, and unpaired Cys residues is likely to contain members which would bind to a target at pH 3.5, 4° C., 50 mM NaCl and release at pH 7.5.

Example 5 illustrates that low salt could be used to foster binding through ionic interactions and that elution with high salt and a different pH will disrupt these interactions.

Example 6 illustrates that binding at pH 8.2, 10 mM NaCl, 25° C. and elution at pH 5.7, 1 M NaCl is likely to elute binding domains that are sensitive to increased ionic strength and lower pH.

Ionic strength can also strongly affect protein-target binding. It is understood that different complexes have different sensitivity to salt. In general, complexes held together by hydrophobic interaction are more stable in high salt, while those held together with ionic interactions are less stable in high salt than they are in low salt. In Example 7, this is exploited by using a library rich in ionic groups, low salt for binding and high salt for elution. Example 8 illustrates that this effect could be seen by binding the library at 5 mM KCl and eluting with saturated KCl. Alternatively, if the library also allows at least some hydrophobic groups, the binding and elution conditions can be reversed, as shown in Example 9. From the same library, it is expected that the binding and elution conditions of Examples 8 and 9 would yield different binding domains for the same target.

Example 10 illustrates that a library allowing hydrophobic groups at many or all of the variable positions of the candidate binding domain is likely to have members that bind tightly in aqueous 1 M NaCl but that release in conditions of 50% by volume ACN/water and no salt. This is because hydrophobic interactions can be disrupted by organic solvent.

Example 11 teaches that domains having several of the amino acids from the group listed in the binding interface would be expected to bind in water and release in 30% MeOH with some salt.

Protein complexes that are primarily held together by hydrophobic interactions are known to "cold denature". Thus, a library that allows the listed hydrophobic residues of Example 12 at many of the varied positions is likely to contain members that will bind a target at 33° C. and high salt and to release at low temperature (e.g., 0° C.) and low salt.

Chaotropes and other solutes can also cause the binding of a stable domain to a target to be very sensitive. Urea typically breaks up interactions between groups that interact through hydrogen bonds. Gin, Ser, Thr, Asn, Tyr, and His are particularly preferred while Asp, Glu, Lys, and Arg are also likely to make interactions that are susceptible to disruption by urea (see Example 13).

The side groups of Asp and Glu are capable of interacting with other acidic groups through chelation of di- or trivalent metal ions, especially $Ca^{++}$, $Mg^{++}$, $Zn^{++}$, $Cu^{++}$, and the like. Carbonyl oxygens in the protein main chain and the side groups of Asn and Gln and the amide nitrogens of a protein main chain and Asn and Gin can also from bonds to certain metal ions. Metal ions can also be sequestered with chelating agents such as EDTA. Thus, in a library that allows Asp and Glu at several surface positions, there are likely to be members that will bind a target that contains acid groups (and does not depend on binding multivalent metal ions for stability) only when a divalent or trivalent metal ion is present in solution (see Example 14). Release of such members can be effected with EDTA or other chelating agents.

Basic side groups can interact with anions such as chloride, acetate, phosphate, sulfate, citrate, or lactate. For multivalent anions, two or more side groups can interact with one ion. Even if such interaction does not greatly stabilize the binding, a polyvalent ion can mask repulsion and allow formation of a complex that would otherwise be unstable. Removal of the polyvalent anion could then cause the complex to dissociate, as illustrated in Example 15.

Table 4 summarizes suitable codons for generating, e.g., in a library providing phage display of binding domain analogues, groups of amino acids that would contribute to the analogues' responsiveness to changes in the listed solution parameters:

TABLE 4

Variegation codons suited to particular separation conditions

| Codon | Amino Acids Allowed | Separation Conditions |
|-------|---------------------|------------------------|
| RNS | IMTNKSRVADEG | change pH, salt, urea, EDTA |
| NAT | YHND | change pH, salt, urea, EDTA |
| NAS | YHQNKDE | change pH, salt, urea, EDTA |
| NRT | YCHRNSDG | change pH, salt, urea, EDTA |
| NYT | SPTAFLIV | organic solvent, low temperature |
| NTT | FLIV | organic solvent, low temperature |
| TNS | FLSYCW | organic solvent, low temperature |
| RRS | NKSRDEG | change pH, salt, urea, EDTA |

EXAMPLE 16

The techniques described above were employed to isolate affinity ligands for recombinant human tissue-type plasminogen activator (tPA). The process of creating tPA affinity ligands involved three general steps: (1) screening of approximately 11 million variants of a stable parental protein domain for binding to tPA, (2) producing small quantities of the most interesting ligands, and (3) chromatographic testing of one ligand bound to activated beads for the affinity purification of tPA from a plasma spiked sample.

For this work, tPA was purchased from CalBiochem (#612200) and immobilized on Reacti-Gel™ agarose beads from Pierce Chemical Company by methods described in Markland et al. (1996). Approximately 200 µg of tPA were coupled to 200 µL of Reacti-Gel™ slurry.

Four libraries of phage-displayed proteins were picked for the screening process. Three were based on the first Kunitz domain of lipoprotein associated coagulation inhibitor (LACI-K1), called Lib#1, Lib#3 and Lib#5, and one was based on *Cucurbida maxima* trypsin inhibitor I(CMTI-I). CMTI-I is a protein found in squash seeds and is able to withstand the acidic and proteolytic conditions of the gut. These proteins each have three disulfide bridges, making them highly constrained and stable. Members of these protein families have been shown to have outstanding thermal stability (>80° C. without loss of activity), outstanding pH stability (no loss of activity on overnight incubation at pH 2 and 37° C. or on 1 hour exposure to pH 12 at 37° C.), and outstanding stability to oxidation. The number of potential amino acid sequences in each library is given in Table 5 below:

TABLE 5

Phage display library populations used in the tPA screening

| Library name | parental domain | Number of members |
|--------------|-----------------|-------------------|
| Lib#1 | LACI-K1 | 31,600 |
| Lib#3 | LACI-K1 | 516,000 |
| Lib#5 | LACI-K1 | 1,000,000 |
| CMTI | CMTI-I | 9,500,000 |
| Total | | 11,000,000 |

The total diversity of the phage-display libraries screened against tPA in this work is estimated to be around 11 million. The Kunitz domain and the CMTI domain could display much greater diversity by varying other parts of their surfaces.

Two screening protocols were used: "slow screen" and "quick screen". In a slow screen, phage from each round were amplified in *E. coli* before the next round. In a quick screen, phage recovered from the target in one round served as the input for the next round without amplification. In a quick screen, both the input and recovered number of phage decreased rapidly over several rounds. The input level can be kept constant in a slow screen. The constant input in a slow screen allows comparisons between rounds that can indicate selection or lack thereof, but comparisons between rounds of quick screens are difficult to interpret. Quick screening increases the likelihood that phage will be selected for binding rather than other irrelevant properties (e.g., infectivity or growth rates).

The phage libraries described were screened for binding to tPA through four rounds. In the first round, the phage libraries were mixed in separate reactions with tPA agarose beads at pH 7 in phosphate-buffered saline (PBS). Bovine serum albumin (BSA) was added at 0.1% to reduce non-specific binding. Unbound phage were washed off at pH 7, and the bound phage eluted at pH 2 for the first screen only. The subsequent three quick screens had a different elution protocol and used pooled outputs of the first screen. Pool A consisted of the combined outputs from the CMTI and Lib#1 libraries, and Pool B consisted of the combined outputs of the Lib#3 and Lib#5 libraries. The binding of pooled libraries was performed at pH 7, however, the first elution to remove bound phage was carried out at pH 5 and a subsequent elution at pH 2 to elute phage that are released in the pH 5–pH 2 range. This was repeated twice more for a total of 4 rounds of selection.

The phage titers from the final three rounds of screening are shown below in Table 6. The output of one round was the input to the next round.

TABLE 6

Phage titers prior to screening and after the last three rounds of screening libraries against tPA

|  | Pool A pH 5 elution | Pool A pH 2 elution | Pool B pH 5 elution | Pool B pH 2 elution |
|---|---|---|---|---|
| Prior to Quick Screening | $7 \times 10^{11}$ | $7 \times 10^{11}$ | $5 \times 10^{11}$ | $5 \times 10^{11}$ |
| After second round | $1 \times 10^{8}$ | $3 \times 10^{7}$ | $7 \times 10^{6}$ | $3 \times 10^{6}$ |
| After third round | $2 \times 10^{5}$ | $2 \times 10^{6}$ | $2 \times 10^{3}$ | $7 \times 10^{3}$ |
| After fourth round | $3 \times 10^{4}$ | $2 \times 10^{5}$ | 150 | 90 |

From the phage titers, it is appears that Pool A converged and contains strong binders, whereas Pool B had neither significant convergence nor strong binders.

Forty phage clones were picked from the third round quick screen selectants of each pool for further analysis, 20 from the pH 5 pool and 20 from the pH 2 pool. The phage DNA was amplified using PCR to determine whether CMTI- or LACI-derived gene fragments were present.

CMTI-derived constructs were found in 38 out of 40 phage isolates from the quick screen of pool A. The remaining isolates did not yield a PCR product, indicating a deletion. Only 10 of the 40 phage isolates from the quick screen of pool B contained the appropriate construct, another indication that the search had not succeeded.

One sign that a particular phage-displayed protein has a high affinity for the target molecule is that it is found repeatedly. From the 18 CMTI-derived phage isolates that released at pH 2, one sequence was found five times, a second, four times, and two of the remaining occurred three times. The 18 sequences formed a closely-related family of selected molecules, a further sign that the search had successfully converged.

Table 7 shows the variability of the observed sequences as a function of the permitted variability and the selection pH. The CMTI library was constructed by introducing combinatorial sequence diversity into codons specifying a surface-exposed loop formed between cysteines 3 and 10 of the parental CMTI protein. The cysteines were not varied because they form an important part of the structure.

TABLE 7

Construction of CMTI Library by Variegation of CMTI-I framework sequence: CMTI-I = RVCPR ILMEC KKDSD CLAEC VCLEH GYCG
(SEQ ID NO: 1)
(see, Dung, L-N. et al., Int'l J. Peptide Protein Res., 34: 492–497 (1989))

| amino acids encoded (SEQ ID NO: 2) | F | Y | S | G | A | R | LSWP QRM TKVA EG | C | FSYC LPHR ITNV ADG |
|---|---|---|---|---|---|---|---|---|---|
| codon position | −5 | −4 | −3 | −2 | −1 | 1 | 2 | 3 | 4 |
| codons (SEQ ID NO: 3) | TTC | TAT | TCC | GGA | GCC | CGT | NNG | TGT | NNT |
| restriction sites or position |  |  | └─AccIII─┘ |  |  |  |  | P3 | P2 |
| amino acids encoded | KRTI | FSYC LPHR ITNV ADG | FSYC LPHR ITNV ADG | LSWP QRM TKVA EG | EKRG | C | K | K | D |
| codon position | 5 | 6 | 7 | 8 | 9 | 10 | 11 | 12 | 13 |
| codons | ANA | NNT | NNT | NNG | RRG | TGT | AAG | AAG | GAT |
| restriction sites or position | P1 | P1' | P2' | P3' |  |  |  |  |  |
| amino acids encoded | S | D | C | L | A | E | C | V | C |
| codon position | 14 | 15 | 16 | 17 | 18 | 19 | 20 | 21 | 22 |
| codons | TCT | GAT | T GC | TTA | GC A | GAA | TGC | GTT | TGC |
| restriction sites or position |  |  | └────EspI────┘ |  |  |  |  |  |
| amino acids encoded | L | E | H | G | Y | C | G | A | G |
| codon position | 23 | 24 | 25 | 26 | 27 | 28 | 29 | 100 | 101 |
| codons | CTC | GAG | CAT | GGT | TAT | TGT | GGC | GCC | GGT |
| restriction sites or position | └──XhoI──┘ |  |  |  |  |  | └── KasI ──┘ |  |  |
| amino acids encoded | P | S | Y | I | E | G | R | I | V |
| codon position | 102 | 103 | 104 | 105 | 106 | 107 | 108 | 109 | 110 |
| codons | CCT | TCA | TAC | ATT | GAA | GGT | CGT | ATT | GTC |
| restriction sites or position |  |  |  |  |  |  |  |  |  |
| amino acids encoded | G | S | A | A | E | . . . rest of mature III |  |  |  |
| codon position | 111 | 112 | 113 | 201 | 202 |  |  |  |  |
| codons | GGT | AGC | GCC | GCT | GAA | . . . rest of coding sequence for III |  |  |  |
| restriction sites or position |  |  |  |  |  |  |  |  |  |

This gives $9.13 \times 10^6$ protein sequences and $16.8 \times 10^6$ DNA sequences.

Table 7 shows the DNA sequence of the CMTI library. Residues $F_{-5}$ and $Y_{-4}$ correspond to residues 14 and 15 in the signal sequence of M13mp 18 from which the recipient phage was engineered. Cleavage by Signal Peptidase I (SP-I) is assumed to occur between $A_{-1}$ and $R_1$. Residues designated 100–113 make up a linker between the CMTI variants and mature III, which begins with residue $A_{201}$. The amino acid sequence $Y_{104}$IEGRIV should allow specific cleavage of the linker with bovine Factor $X_a$ between $R_{108}$ and $I_{109}$. The M13-related phage in which this library was constructed carries an aropicillin-resistance gene ($Ap^R$) so that cells infected by library phage become Ap resistant. At each variable amino acid position, the wildtype amino acid residue is shown underscored. The amino acid sequence shown in Table 7 is designated SEQ ID NO: 2; the nucleotide sequence shown in Table 7 is designated SEQ ID NO: 3. In those sequences, amino acids 1–29 of SEQ ID NO: 3 represent the CMTI-derived polypeptide analogues; nucleotides 16–102 of SEQ ID NO: 2 code for the CMTI-derived polypeptide.

The isolates obtained from the pH 5 selection procedure exhibited greater sequence diversity than did the pH 2 selectants (Table 8). Despite the greater sequence variability, pH 5 selectants comprised a family of closely-related protein sequences. Forming all combinations of the amino-acid types observed at each position gives only 13,400 (=2×4× 3×4×7×5×4) which is 0.15% of the population. In the 20 sequences determined, there were four sequences that occurred more than once, suggesting that the actual diversity is less tand 13,400. Although the family of pH 5-selected sequences is clearly related to the pH 2-selected family, there was only one example of sequence identity between the two sequence populations.

TABLE 8

Reduction in variability at positions in CMTI upon selection for binding to tPA

| Position: | 2 | 3 | 4 | 5 | 6 | 7 | 8 | 9 | 10 |
|---|---|---|---|---|---|---|---|---|---|
| Permitted Variability | 13 | C | 15 | 4 | 15 | 15 | 13 | 4 | C |
| Variability of pH 5 Selectants | 2 | C | 4 | 3 | 4 | 7 | 5 | 4 | C |
| Variability of pH 2 Selectants | 1 | C | 1 | 2 | 3 | 3 | 1 | 2 | C |

At positions 6 and 7, most (12 of 15) allowed amino acid types were rejected in the pH 2 selectants. From the selected sequences, it is not clear whether the selected amino acids at positions 6 and 7 contributed to binding or merely represent the elimination of unacceptable possibilities at these positions.

The powerful convergence of the selection process is particularly evident for the pH 2 selectants at positions 2, 4 and 8, where, although many amino acid types could occur, only one amino acid type was found. This is a strong indication that this specific amino acid is critical to binding. At each of these positions, the uniquely selected type of the pH 2 population was also the most common type at that position in the pH 5 population. Allowing all observed amino acid types at each position of the pH 2 pool gives only 36 sequences, 0.0004% of the initial population. That several sequences appeared more than once suggests the number of different sequences present in the pH 2 pool is not larger than 36.

Table 9 shows the amino acid sequences of the variegated region (amino acid positions 1–12) for the 38 sequenced analogues of CMTI-I. The appearance of methionine residues at a position not designed to be varied (position 11) indicates a DNA synthesis error in formation of the library.

TABLE 9

First twelve amino acids of isolated CMTI-I analogues

| AMINO ACID position | 1 | 2 | 3 | 4 | 5 | 6 | 7 | 8 | 9 | 10 | 11 | 12 | SEQ ID |
|---|---|---|---|---|---|---|---|---|---|---|---|---|---|
| CMTI-I | R | V | C | P | R | I | L | M | E | C | K | K | 1 |
| 101 | R | W | C | P | K | T | S | L | G | C | M | K | 4 |
| 102 | R | L | C | P | K | T | Y | L | G | C | M | K | 5 |
| 103 | R | W | C | S | T | Y | S | L | G | C | M | K | 6 |
| 104 | R | W | C | S | T | Y | S | L | G | C | M | K | 7 |
| 105 | R | L | C | P | K | T | S | L | E | C | M | K | 8 |
| 106 | R | W | C | S | T | Y | S | L | G | C | M | K | 9 |
| 107 | R | L | C | P | K | T | S | L | E | C | M | K | 10 |
| 108 | R | W | C | S | K | S | S | L | E | C | M | K | 11 |
| 109 | R | L | C | P | K | T | D | L | G | C | M | K | 12 |
| 110 | R | W | C | P | K | S | S | M | G | C | K | K | 13 |
| 111 | R | W | C | P | R | T | V | Q | E | C | M | K | 14 |
| 112 | R | W | C | P | T | A | P | L | E | C | M | K | 15 |
| 113 | R | L | C | P | K | T | D | L | G | C | M | K | 16 |
| 114 | R | W | C | P | K | S | A | L | D | C | K | K | 17 |
| 115 | R | W | C | T | K | T | S | R | E | C | M | K | 18 |
| 116 | R | W | C | I | R | T | D | L | G | C | M | K | 19 |
| 117 | R | W | C | P | K | T | S | L | G | C | M | K | 20 |
| 118 | R | W | C | P | R | T | V | R | R | C | M | K | 21 |
| 119 | R | W | C | P | K | T | H | K | E | C | M | K | 22 |
| 120 | R | W | C | P | K | T | S | L | E | C | M | K | 23 |
| 221 | R | W | C | P | K | S | T | L | G | C | M | K | 24 |
| 222 | R | W | C | P | K | S | T | L | G | C | M | K | 25 |
| 223 | R | W | C | P | K | Y | T | L | E | C | M | K | 26 |
| 224 | R | W | C | P | R | S | S | L | E | C | M | K | 27 |
| 225 | R | W | C | P | K | Y | T | L | E | C | M | K | 28 |
| 226 | R | W | C | P | R | S | N | L | E | C | M | K | 29 |
| 227 | R | W | C | P | R | S | N | L | E | C | M | K | 30 |
| 228 | R | W | C | P | K | Y | T | L | E | C | M | K | 31 |
| 229 | R | W | C | P | K | Y | T | L | E | C | M | K | 32 |
| 230 | R | W | C | P | K | Y | T | L | E | C | M | K | 33 |
| 231 | R | W | C | P | R | S | T | L | E | C | M | K | 34 |
| 232 | R | W | C | P | K | T | S | L | G | C | M | K | 35 |
| 233 | R | W | C | P | K | Y | T | L | E | C | M | K | 36 |
| 234 | R | W | C | P | R | S | L | E | C | M | K | | 37 |
| 235 | R | W | C | P | K | S | T | L | G | C | M | K | 38 |
| 236 | R | W | C | P | R | S | S | L | E | C | M | K | 39 |
| 237 | R | W | C | P | R | S | N | L | E | C | M | K | 40 |
| 238 | R | W | C | P | R | S | N | L | E | C | M | K | 41 |

In table 9, analogues having the sequences designated 101–120 were obtained by elution at pH 5 and analogues having the sequences 221–238 were obtained by fractionation at pH 2.

The specificity of phage-bound ligand candidates was tested by determining their affinity for other immobilized proteins. The phage-bound proteins showed no affinity for the related human serum proteases plasmin and thrombin bound to beads (data not shown). Additionally, experiments were performed on the phage isolates to determine relative affinity for and release characteristics from immobilized tPA.

In the case of the pH 5-releasing phage isolates, the majority of the phage are released at pH 5 and an order of magnitude fewer are released by further dropping the pH to 2. This indicates suitable affinity ligands with a relatively clean release upon lowering the pH to 5. In the case of the pH 2 releasing isolates, only isolate #232 gave a truly selective binding at pH 5 and then release at pH 2.

Ligand Synthesis and Immobilization

Next, free CMTI-derivative polypeptides were synthesized using the sequence information determined from the DNA of the phage isolates. Although the CMTI derivatives (analogues) could have been readily chemically synthesized, it was decided to express the polypeptides in yeast. One of the pH 5-releasing isolates, #109 (Table 9; ref. SEQ ID NO. 12), and one of the pH 2-releasing isolates, #232 (Table 9;

ref. SEQ ID NO. 35), were selected for expression in *Pichia pastoris*. At positions 4 and 8, isolate #109 has the same amino acid types as seen in the pH 2 selectants; at position 2, isolate #109 differs from the pH 2 selectants.

The appropriate gene constructs were synthesized and inserted into the *Pichia pastoris* expression system (Vedvick et al., 1991 and Wagner et al., 1992) to create production strains. Five-liter fermentations of each strain resulted in high-level expression. It was estimated that the proteins were secreted into the fermentation broth in excess of 1 g/L. The crude fermentation suspensions were clarified by centnfbgtion, and $0.2\mu$ mnicrofiltration steps. The $0.2\mu$ filtrates were purified by ultrafiltration using PTTK cassettes with a 30 kDa NMWL cutoff. The ligands were purified from the ultrafiltration filtrates by cation exchange chromatography with Macro-Prep High S cation exchange support (BioRad), followed by two reversed-phase separations. The reversed-phase separations used a linear gradient starting with water containing 0.1% TFA and having increasing acetonitrile (containing 0.1% TFA) which was increased to 50% at 90 minutes. The resulting protein was more than 95% pure as measured by PDA spectral analysis on a 5 $\mu$m reversed phase column.

The ligand candidate was immobilized on a bis-acrylamide/azlactone copolymer support with immobilized diaminopropylamine (Emphaze Ultralink™; Pierce Chemical Co.) according to the manufacturer's instructions. About 30 mg of CMTI analogue #109 were coupled to 1 mL of the activated chromatography support.

Column Testing

A Waters AP Minicolumn, 5.0 cm×0.5 cm ID nominal dimensions was modified by the addition of a second flow adaptor which allowed the column length to be reduced to 2.5 cm. This column was packed with #109-Emphaze Ultralink™ beads using the recommended protocol and washed using a series of increasing NaCl concentration washes at pH 7 concluding with a 1 M wash.

In a first test of the #109 affinity column tissue-type plasminogen activator obtained from CalBiochem was made up to manufacturer's specifications to provide a 1 mg/mL solution of tPA. Coagulation Standard (Coagulation Control Level 1 from Sigma Diagnostics, Catalog #C-7916) lyophilized human plasma, was reconstituted according to the manufacturer's instructions, then diluted 10× and the tPA added. This sample was loaded onto the column and eluted in the presence of 1 M NaCl in all buffers, which was sufficient to suppress non-specific protein binding to the column and to permit the pH-controlled binding and release of the tPA. There were two distinct peaks: The first contained the plasma proteins (which were not retained on the column); the second, obtained after lowering the pH, contained the tPA, without any contaminating plasma components. The results were confirmed by silver stained gel (not shown). 90% of the tPA product was recovered.

A second affinity column using the #109 CMTT analogue was prepared using EAH Sepharose 4B™ agarose beads (Pharmacia; Upsala SE) as the chromatography support. The separation was performed on an HPLC system manufactured by Waters Inc. (Milford, Mass.). The system comprised a Model 718 Autoinjector, a Model 600 solvent delivery system with pumpheads capable of delivering 20 mL/minute, and a Model 996 photodiode array detector. All of the equipment was installed according to manufacturer's specifications. The system was controlled by a Pentium 133IBM-compatible computer supplied by Dell Corp. The computer was furnished with a 1 gigabyte hard drive, 16 megabytes of RAM, and a color monitor, onto which the Millenium software supplied by Waters Inc. was loaded.

Spectral data in the range 200 nm to 300 nm were collected with 1.2 nm resolution. FIGS. 1, 2, 3, and 4 were collected at 280 nm. The mobile phases for the chromatographic work were Buffer A and Buffer B: Buffer A consisted of 25 mM potassium phosphate, 50 mM arginine, and 125 mM NaCl, buffered to pH 7 with potassium hydroxide. Buffer B consisted of 50 mM potassium phosphate and 150 mM NaCl, buffered to pH 3 with phosphoric acid. In all cases, samples were injected in 100% Buffer A, followed by washing with 100% Buffer A from t=0 to t=2 min. From t=2 min. to t=8 min., elution was with 100% Buffer B. After t=8 min., elution was with 100% Buffer A. The gradient delay volume of the HPLC system was approximately 4 mL and the flow rate was 0.5 mL/min.

tPA from another commercial source was made up to manufacturer's specifications to provide a 1 mg/mL solution. Coagulation Standard (Coagulation Control Level 1 from Sigma Diagnostics, Catalog #C-7916), lyophilized human plasma, was reconstituted according to the manufacturer's instructions. This solution was diluted 10:1 to obtain a solution having roughly 10 times the absorbance of the tPA solution.

Figure 3:
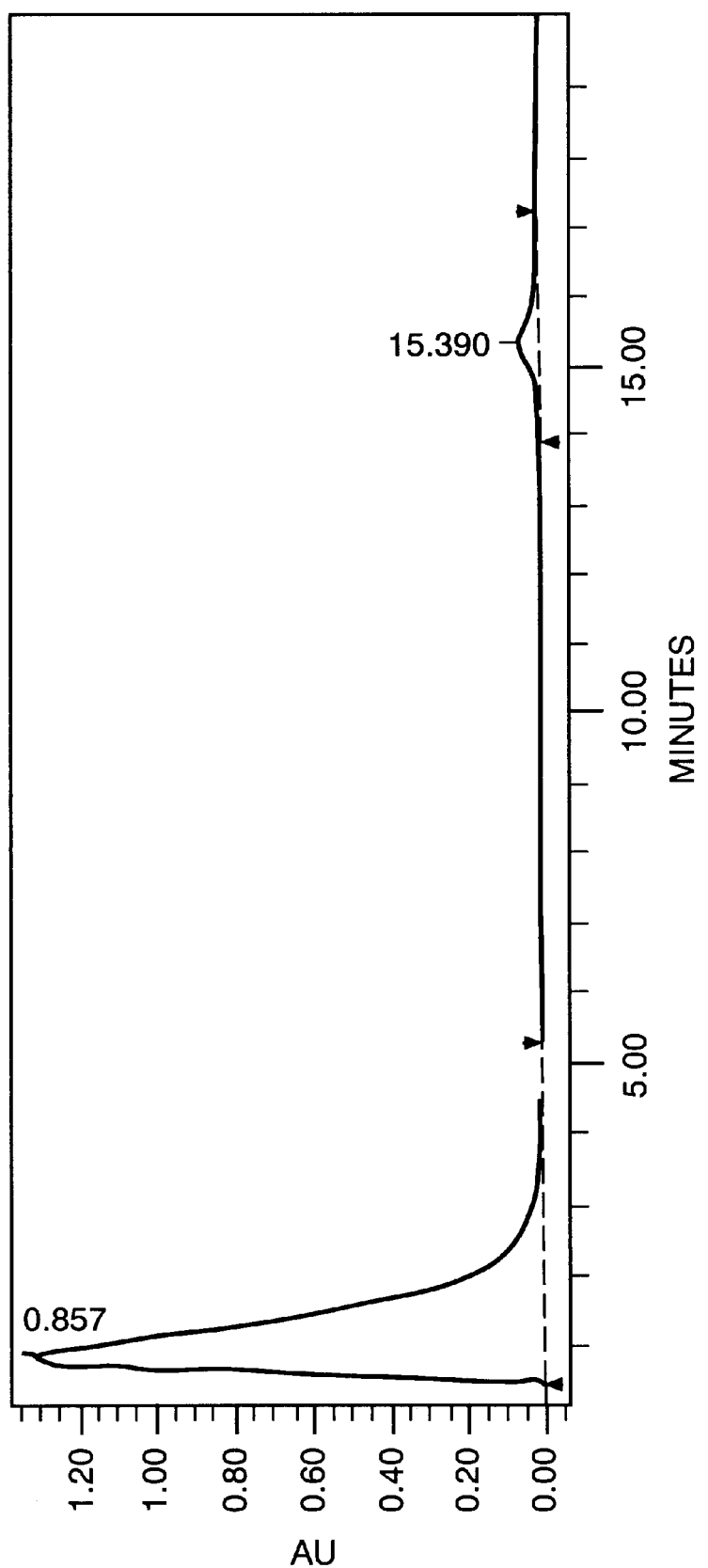
FIG. 3 shows a chromatogram of a mixture consisting of 25 μL of Coagulation Standard (Diluted 10×) spiked with 25 μL of tPA, with elution over a pH 7–pH 3 gradient. The peak at 1 minute is the collection of plasma proteins and the peak at 15.4 minutes is the tPA.
Figure 4:
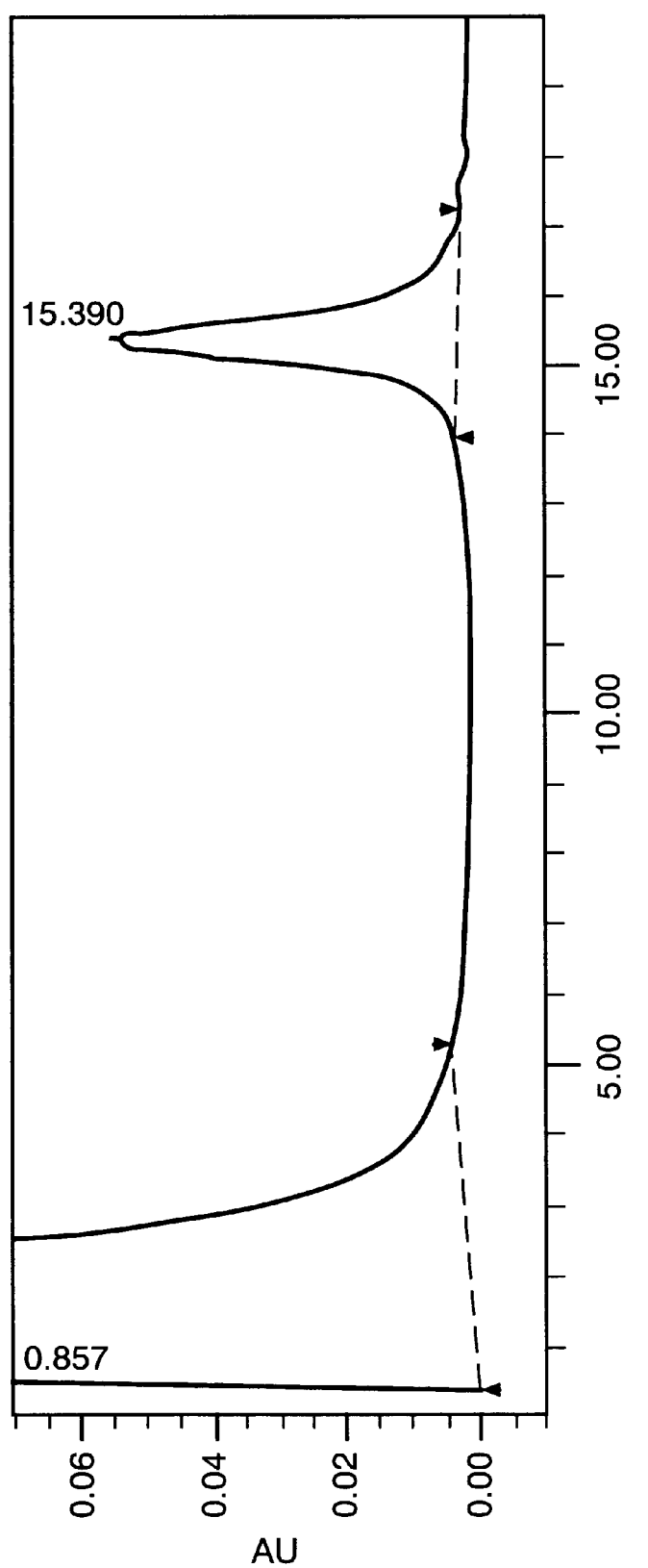
FIG. 4 shows the same chromatogram as shown in FIG. 3 with vertical scale expanded.

In the test shown in FIG. 1, a sample of pure tPA (25 $\mu$L of 1 mg/mL tPA) was run over the #109 CMTI derivative-contaiing column and eluted as described above. The chromatogram shows sharp elution of about 90% of the tPA material after about 15 min. In the test shown in FIG. 2, a sample of Coagulation Standard (10× dilution) was run over the #109 CMTI derivative-containing column with elution conditions as described above. Virtually all the material eluted immediately from the column (was not retained). In the test separation shown in FIGS. 3 and 4, a sample contaig tPA added to human plasma standard was loaded onto the column and eluted as described above. As can be seen in FIGS. 3 and 4, the tPA was retained and the plasma proteins eluted in the void volume. Bound tPA was released at about 15.4 minutes. It was estimated that the tPA was released at about pH 4. The tPA peak was collected and examined using a silver-stained, reducing SDS-polyacrylamide gel, and, when compared with the starting material, was found to be>95% pure.

EXAMPLE 17

The tPA affinity ligands isolated from the CMTI library were examined further in order to design additional candidate domains that might bind to tPA as well.

As noted above, almost all of the variegation in amino acid positions used in building the CTMI library occurred between two cyteines at positions 3 and 10 of CMTI-I (see Table 3). In the parental CMTI protein, these cysteines form disulfide bonds with other cysteine residues elswhere in the protein (see SEQ ID NO: 1), however with the successful isolation of affinity ligands from the CMTI library, a secondary library was conceptualized which was based on variegating a truncated 15-amino acid segment of the isolate #109 (see amino acids 1–15 of SEQ ID NO: 12). If the $C_3$ and $C_{10}$ cysteines of these members formed a disulfide bond, then a constrained loop having tPA binding properties might be obtained. Initial studies with the 15-amino acid segment derived from affinity ligand isolate #109 bound to a chromatographic support indicated that the $C_3$–$C_{10}$ loop formed and that the immobilized loop bound to tPA.

The foregoing experiments point to two new families of tPA affinity ligands isolated in accordance with this invention, comprising polypeptides including the sequences:

Arg-$X_1$-CYS-$X_2$-$X_3$-$X_4$-$X_5$-$X_6$-$X_7$-Cys-$X_8$-Lys-Asp-Ser-Asp-Cys-Leu-Ala-Glu-Cys-Val-Cys-Leu-Glu-His-Gly-Tyr-Cys-Gly (SEQ ID NO: 42) and Arg-$X_1$-Cys-$X_2$-$X_3$-$X_4$-$X_5$-$X_6$-$X_7$-Cys-$X_8$ (SEQ ID NO: 43), wherein $X_1$ is Trp or Leu; $X_2$ is Pro, Ser, Thr or Ile; $X_3$ is Arg, Lys or Thr; $X_4$ is Ser, Tyr, Thr or Ala; $X_5$ is Ser, Tyr, Asp, Val, Pro, Ala, His, Asn or Thr; $X_6$ is Leu, Met, Gln, Arg or Lys; $X_7$ is Glu, Gly or Arg; and $X_8$ is at least Lys or Met. Since the presence of Met residues at position 11 in the sequence was not planned but turned out to be favored for binding to tPA, it is likely that other amino acids, for instance other non-polar amino acids such as Ala, Val, Leu, Ble, Phe, Pro or Trp substituted at position 11 will provide additional tPA-binding analogues.

EXAMPLE 18

This example illustrates the isolation of affinity ligands useful in the separation of a target humanized monoclonal antibody from a feed stream of clarified goat's milk.

The target purified humanized monoclonal antibody of IgG isotype and unknown specificity was supplied by the producer and stored in 500 µg aliquots in 50 µL PBS at −70° C. Polyclonal goat IgG was purchased from Cappel.

Varying amounts (i.e., 1 µg, 500 µg, 200 µg, 100 µg, 50 µg and 0 µg) of the humanized monoclonal antibody (hMAb), made to 100 µL with PBS, were each added to three wells of an Immulon 2 plate and incubated overnight at 4° C. The wells were washed three times with 200 µL PBS with 0.1% non-ionic detergent (Tween 20), then blocked with 100 µL PBS with 1% BSA per well for 1 hour at 4° C. Plates were tested using goat anti-human gG-HRP (CalBiochem) developed with OPD substrate solution (SigmaFast #9187, Sigma Chemical Co.), quenched with 4M $H_2SO_4$, and $A_{490}$ read in a Bio-Tek microtiter plate reader.

For the screen, polyclonal goat IgG was used as a competitive binder. The screening was carried out using three phage display libraries: CMn, TN-6/I and TN-10/V. The construction of CMII is given above (Table 7). The peptide construction of TN-6/I and TN-10/V is given below (Table 10 and Table 11, respectively). In the following tables, the encoded amino acids of the variegated, phage-displayed polypeptide domain are shown. DNA encoding the polypeptides was inserted into M13 gene iii in as similar manner as described above with respect to the CMTI library.

TABLE 10

Construction of TN-6/I Library by Variegation of Microprotein-6 framework sequence: AEG$X_1$C $X_1X_2X_2X_1$C $X_1$SY
(SEQ ID NO: 44)
$X_1$ = ACDFGHILNPRSTVY
$X_2$ = AEGKLMPQRSTVW

| amino acids encoded (SEQ ID NO: 44) | A | E | G | ACDF GHIL NPRS TVY | C | ACDF GHIL NPRS TVY | AEGK LMP QRST VW | AEGK LMP QRST VW | ACDF GHIL NPRS TVY |
|---|---|---|---|---|---|---|---|---|---|
| amino acid position | 1 | 2 | 3 | 4 | 5 | 6 | 7 | 8 | 9 |
| amino acids encoded | C | ACDF GHIL NPRS TVY | S | Y | | | | | |
| amino acid position | 10 | 11 | 12 | 13 | | | | | |

This library design gives 8.55 × 10$^6$ protein sequences and 17 × 10$^6$ DNA sequences.

TABLE 11

Construction of TN-10/V Library by Variegation of Microprotein-10 framework sequence: AEGA$X_1$ C$X_2X_3X_1X_4$ $X_3X_3X_5X_2$C $X_1$GP
(SEQ ID NO: 45)
$X_1$ = DFHILNVY
$X_2$ = ADGHLPRV
$X_3$ = AEGLPQRV
$X_4$ = FIKLMNY
$X_5$ = IKMNRST

| amino acids encoded (SEQ ID NO: 45) | A | E | G | A | DFHI LNVY | C | ADG HLPR V | AEGL PQRV | DFHI LNVY |
|---|---|---|---|---|---|---|---|---|---|
| amino acid position | 1 | 2 | 3 | 4 | 5 | 6 | 7 | 8 | 9 |
| amino acids encoded | FIKL MNY | AEGL PQRV | AEGL PQRV | IKMN RST | ADG HLPR V | C | DFHI LNVY | G | P |
| amino acid position | 10 | 11 | 12 | 13 | 14 | 15 | 16 | 17 | 18 |

This library design gives 8.2 × 10$^8$ protein sequences and 1.1 × 10$^9$ DNA sequences.

Four rounds of screening were completed. The binding screen was performed at neutral pH and approximately 80 mM NaCl with 1% polyclonal goat IgG in the binding solution as a competitive binder. Elution was performed with a pH switch.

The binding conditions for all rounds were: incubation at room temperature (RT) for 2 hours in ½×PBS (½ concentration PBS), 0.1% BSA, 1% goat IgG. The wash and elution conditions for each round are summarized in Table 12.

TABLE 12

Washes and Elution Conditions

| Step | Screening Round # | | | |
|---|---|---|---|---|
| | 1 | 2 | 3 | 4 |
| Wash: 15 times rapidly at RT with ½× PBS, 0.1% Tween 20 | yes | yes | yes | yes |
| Wash: 10 min. at RT with ½× PBS, 0.1% BSA | no | no | yes | yes |
| Elute: 2 times 5 min. at RT with 50 mM citrate, 150 mM NaCl, 0.1% BSA, pH 5 | no | yes | yes | yes |
| Elute: 2 times 5 min. at RT with 50 mM citrate, 150 mM NaCl, 0.1% BSA, pH 2 | yes | yes | yes | yes |

After each round, the phage eluted were counted and then amplified by transduction. pH 5 and pH 2 eluates were amplified separately after Round 2 and kept separate during successive screens, so that the pH 2 eluates selected candidates that did not release at pH 5. Table 13 below shows the convergence of the screen over the four rounds for TN-6/I at pH 2, for TN-10/V at pH 2, for CMTI at pH 2, and for CMTI at pH 5.

TABLE 13

Ave. fraction of input phage contained in each round of screening against hMAb

| Round # | TN-6/I pH 5 eluate | TN-6/I pH 2 eluate | TN-10/V pH 5 eluate | TN-10/V pH 2 eluate | CMTI pH 5 eluate | CMTI pH 2 eluate |
|---|---|---|---|---|---|---|
| 1 | N/A | $4 \times 10^{-6}$ | N/A | $4 \times 10^{-6}$ | N/A | $7 \times 10^{-6}$ |
| 2 | $9 \times 10^{-6}$ | $7 \times 10^{-6}$ | $9 \times 10^{-6}$ | $5 \times 10^{-6}$ | $8 \times 10^{-6}$ | $7 \times 10^{-6}$ |
| 3 | $3 \times 10^{-6}$ | $1 \times 10^{-6}$ | $2 \times 10^{-6}$ | $1 \times 10^{-6}$ | $8 \times 10^{-6}$ | $6 \times 10^{-6}$ |
| 4 | $4 \times 10^{-6}$ | $2 \times 10^{-5}$ | $3 \times 10^{-6}$ | $7 \times 10^{-5}$ | $2 \times 10^{-4}$ | $5 \times 10^{-4}$ |

From each of the four convergent screens, approximately 12 phage isolates were selected for premliminary sequencing. In all but the TN-10/V isolates, a significant homology amongst the selectants was seen. For example, the twelve CMTI pH5 isolates selected for sequencing collapsed to 3 DNA sequences and 2 amino acid sequences. From the sequenced selectants, 16 candidates were selected for characterization of the relative binding affinity, specificity and pH-release characteristics of the phage-bound proteins for the target hMAb, using pH 2 as the release test. The test involved immobilization of the target hMAb, polyclonal goat IgG, and BSA to microtiter plates, followed by detection of relative binding of the phage using a biotinylated sheep anti-M13 antibody ELISA kit from 5 Prime→3 Prime, Inc. (Boulder, Colo. US).

The phage isolates tested had the following designations:
from TN-6/I, pH 2 release: T41, T42, T48, T49, T52
from TN-10/V, pH 2 release: T61, T64, T66, T70, T72, T74, T75
from CMTI, pH 5 release: C21, C22, C23
from CMTI, pH 2 release: C3

Figure 5:
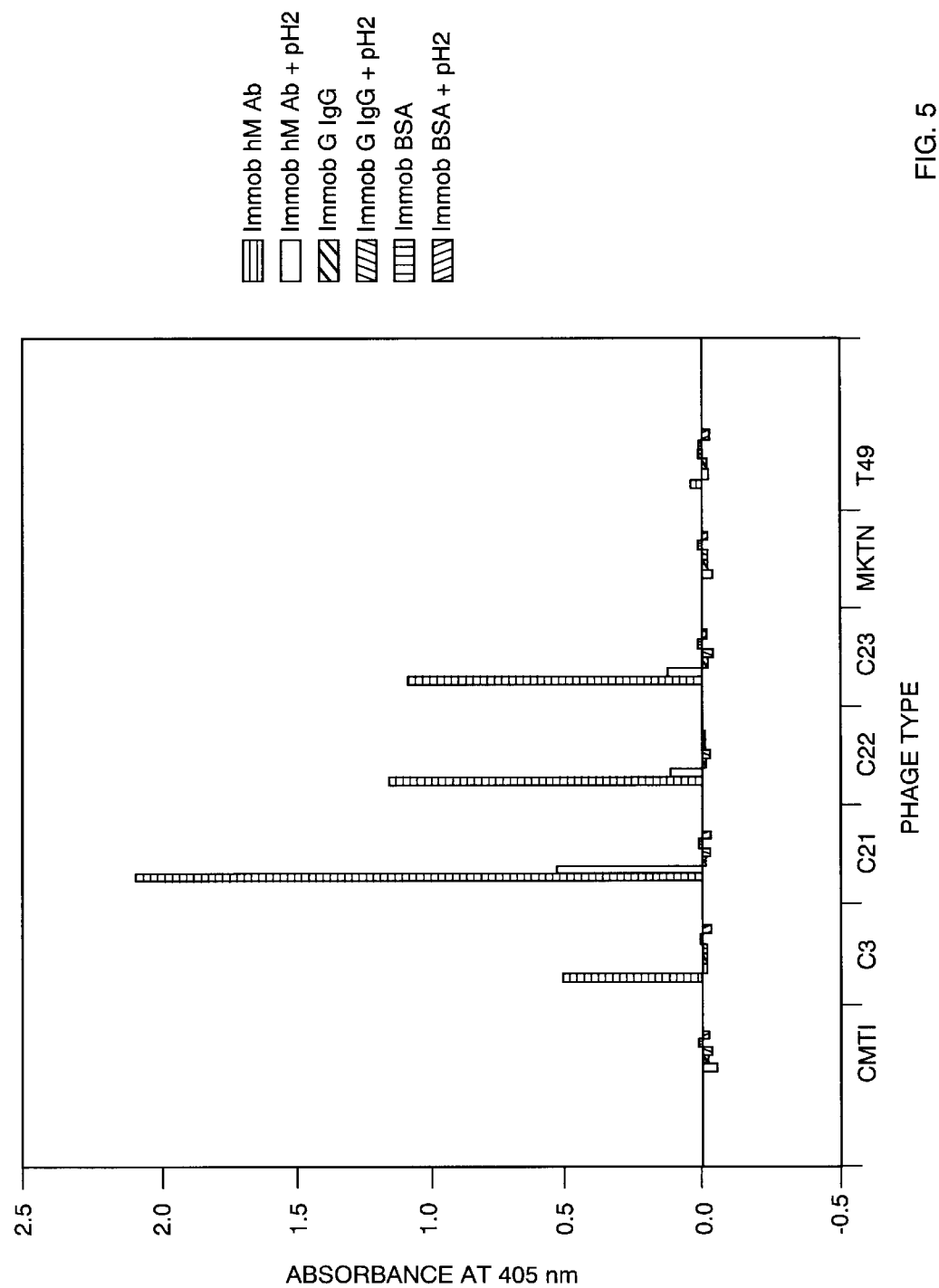
FIG. 5 shows the results of an ELISA testing the binding of the CMTI phage isolates C3, C21, C22, C23, and a TN-6/I phage isolate T49 (see Example 18 infra) against an immobilized human monoclonal antibody target at pH 7, an immobilized human monoclonal antibody target at pH 2, immobilized goat IgG at pH 7, immobilized goat IgG at pH 2, immobilized BSA at pH 7, and immobilized BSA at pH 2. The ELISA identifies affinity ligands useful for separation of the humanized antibody from a feed stream including goat antibodies.
Figure 6:
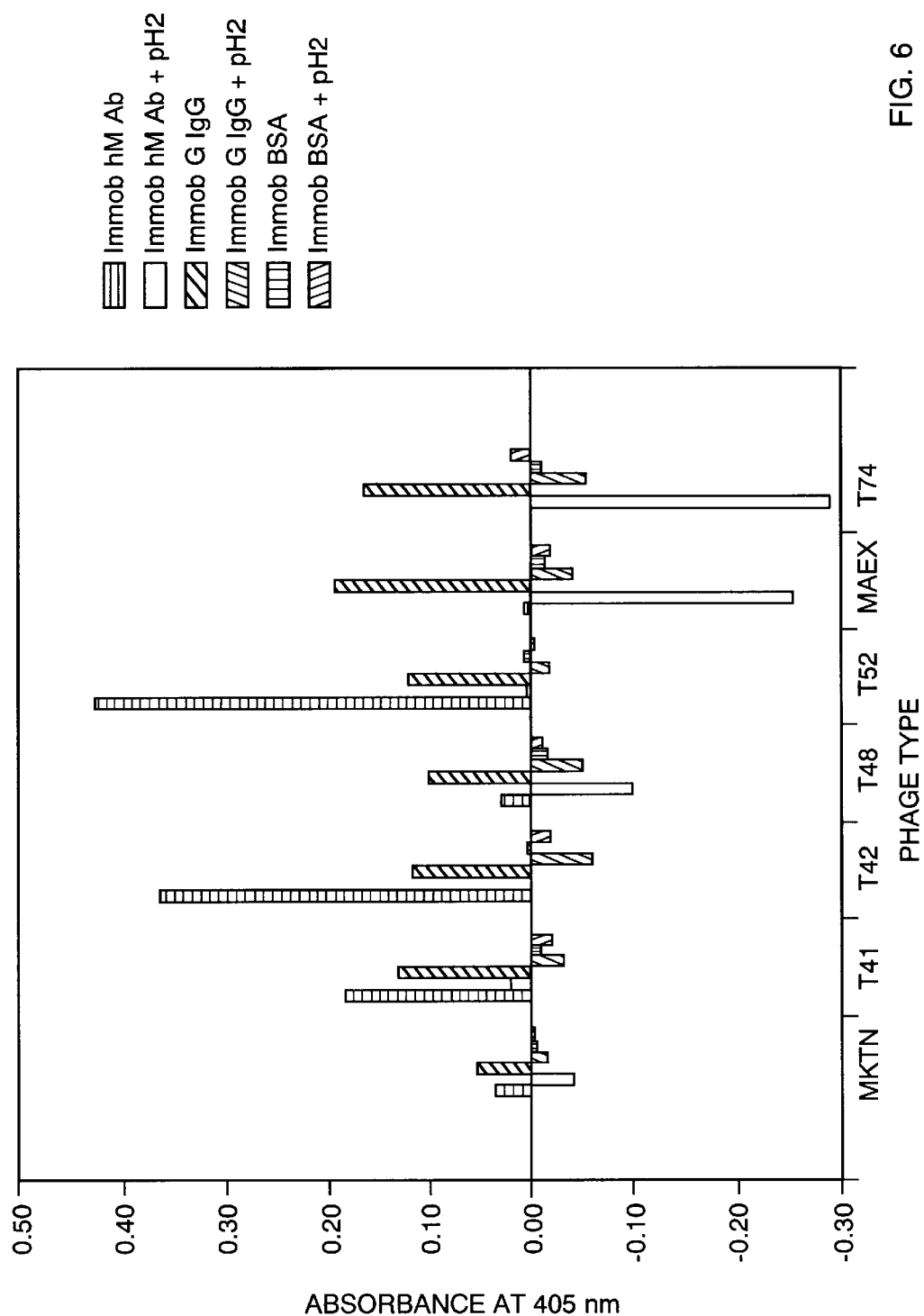
FIG. 6 shows the results of an ELISA testing the binding of the TN-6/I phage isolates T41, T42, T48, T52 and T74 (see Example 18 infra) against an immobilized human monoclonal antibody target at pH 7, an immobilized human monoclonal antibody target at pH 2, immobilized goat IgG at pH 7, immobilized goat IgG at pH 2, immobilized BSA at pH 7, and immobilized BSA at pH 2. The ELISA identifies affinity ligands useful for separation of the humanized antibody from a feed stream including goat antibodies.
Figure 7:
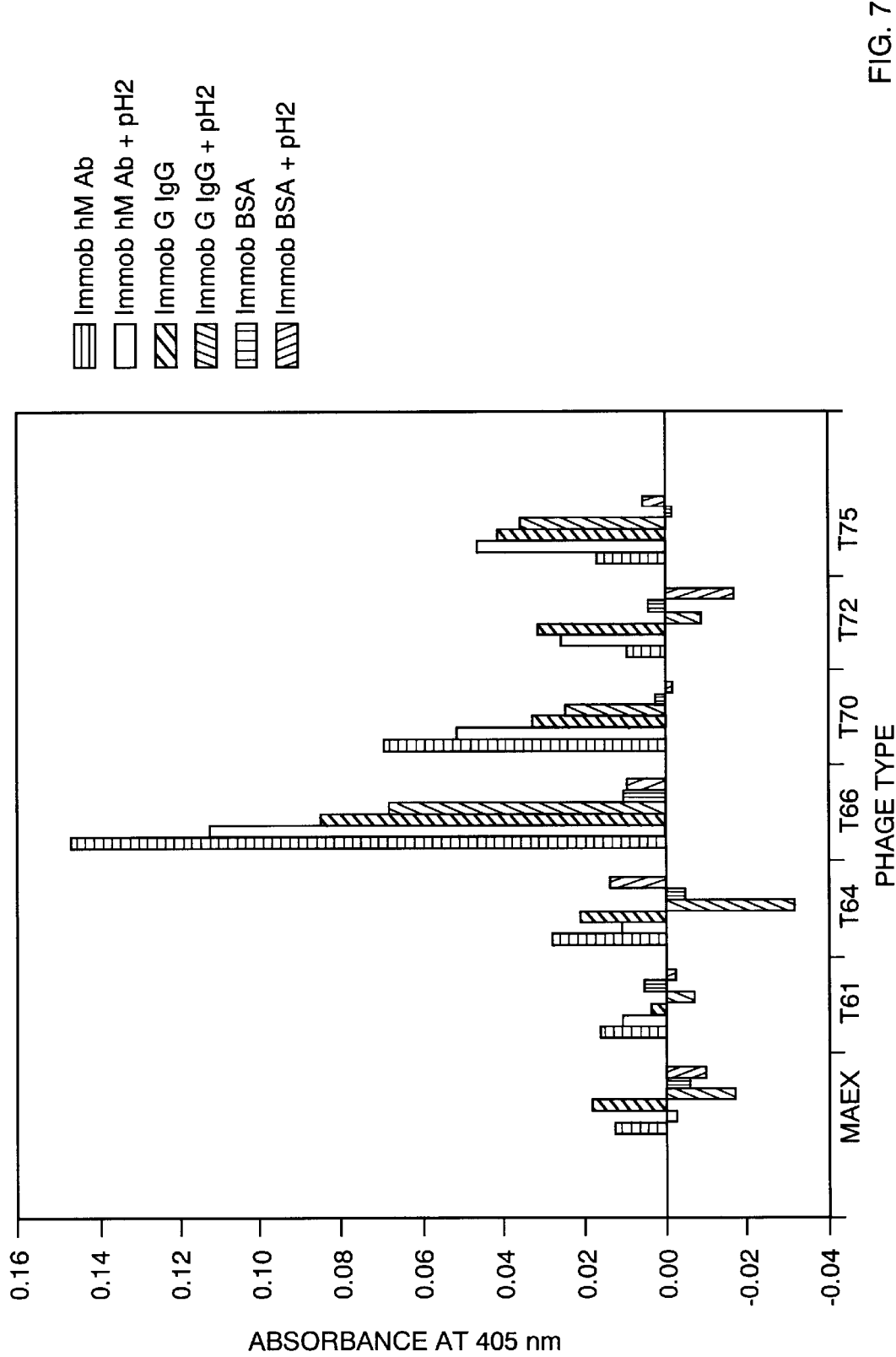
FIG. 7 shows the results of an ELISA testing the binding of the TN-10/V phage isolates T61, T64, T66, T70, T72 and T75 (see Example 18 infra) against an immobilized human monoclonal antibody target at pH 7, an immobilized human monoclonal antibody target at pH 2, immobilized goat IgG at pH 7, immobilized goat IgG at pH 2, immobilized BSA at pH 7, and immobilized BSA at pH 2.
Figure 8:
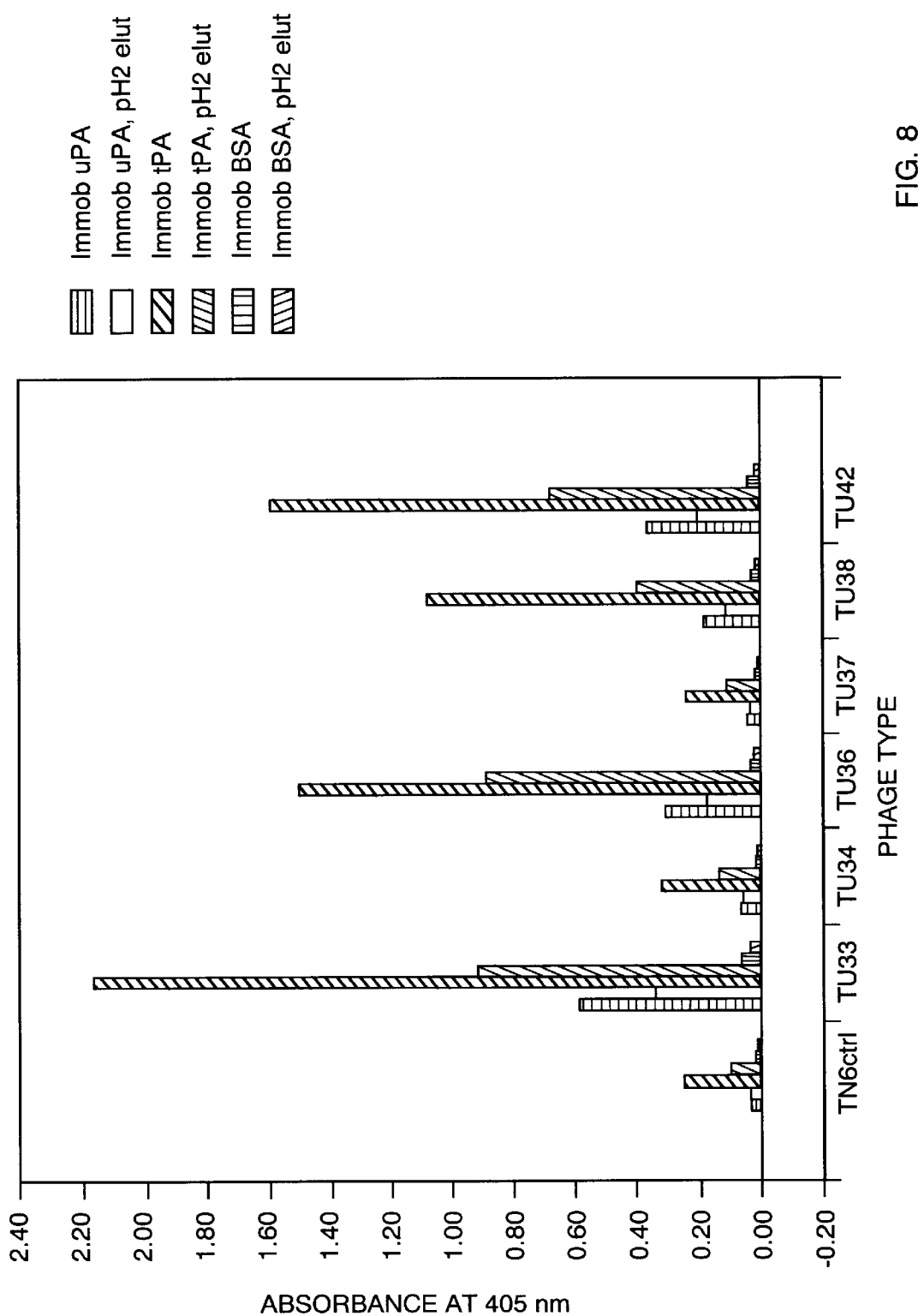
FIG. 8 shows the results of an ELISA testing the binding of the TN-6/I phage isolates having urkinase binding affinity from four rounds of screening; TU33, TU34, TU36, TU37, TU39 and TU42 (see Example 19 infra) against immobilized urokinase at pH 7, immobilized urokinase at pH 2, immobilized tPA at pH 7, immobilized tPA at pH 2, immobilized BSA at pH 7, and immobilized BSA at pH 2. The ELISA identifies affinity ligands useful for separation of urokinase from a feed stream such as urine.
Figure 9:
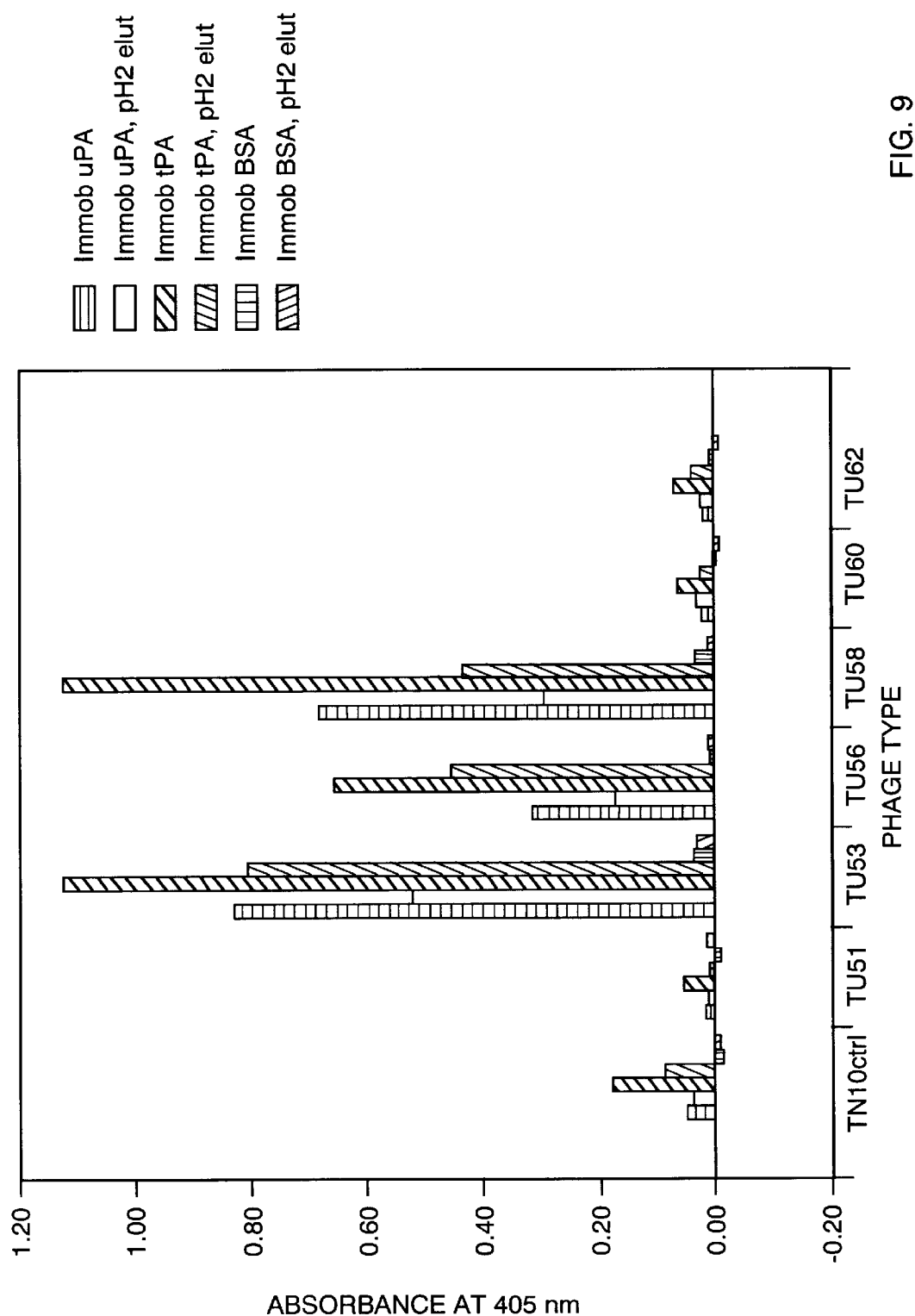
FIG. 9 shows the results of an ELISA testing the binding of some of the TN-10/VIIIa phage isolates having urkinase binding affinity from four rounds of screening: TU51, TU53, TU56, TU58, TU60 and TU62 (see Example 19 infra) against immobilized urokinase at pH 7, immobilized urokinase at pH 2, immobilized tPA at pH 7, immobilized tPA at pH 2, immobilized BSA at pH 7, and immobilized BSA at pH 2. The ELISA identifies affinity ligands useful for separation of urokinase from a feed stream such as urine.
Figure 10A:
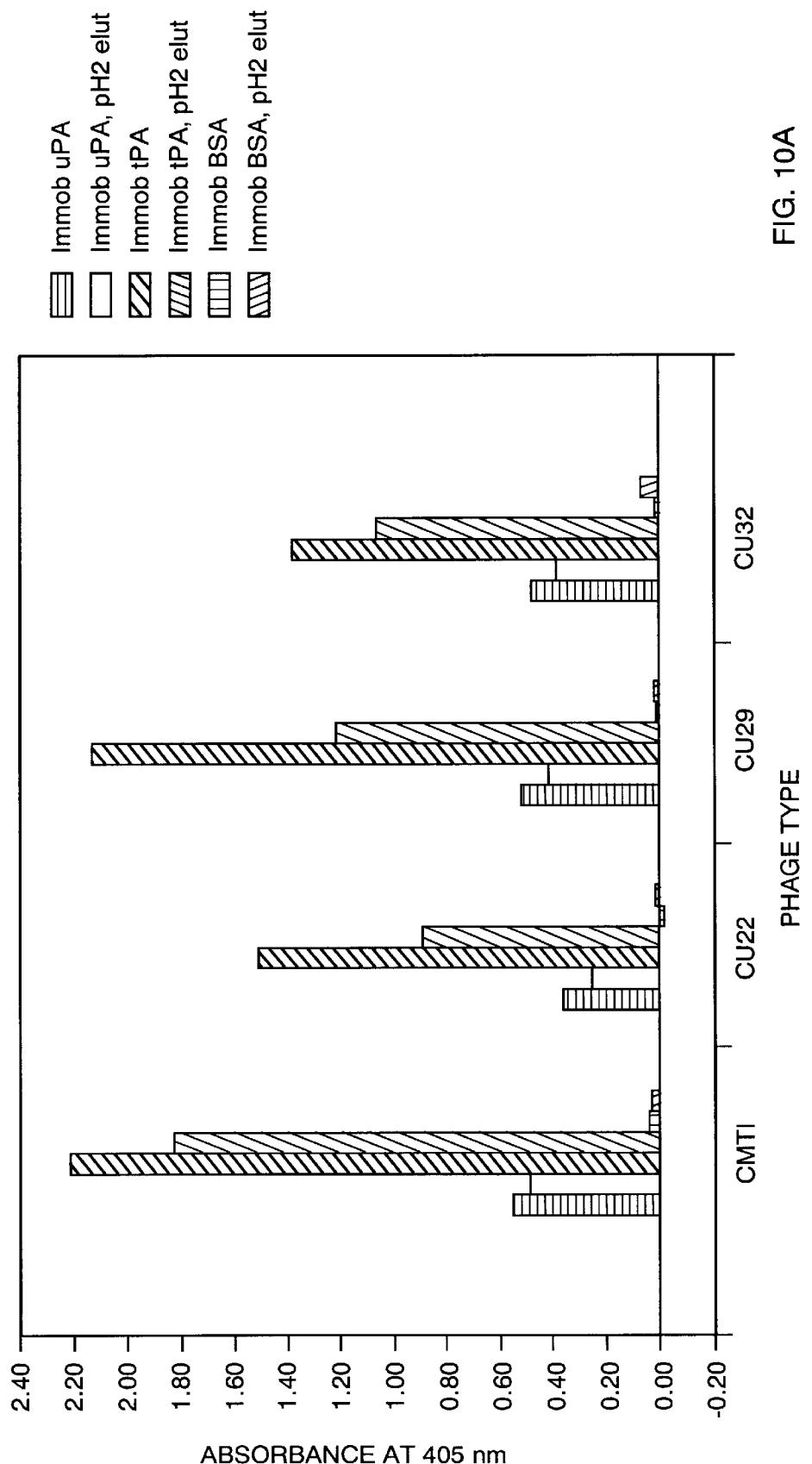
FIG. 10A shows the results of an ELISA testing the binding of some of the CMTI phage isolates having urkinase binding affinity from four rounds of screening: CU22, CU29, and CU32 (see Example 19 infra) against immobilized urokinase at pH 7, immobilized urokinase at pH 2, immobilized tPA at pH 7, immobilized tPA at pH 2, immobilized BSA at pH 7, and immobilized BSA at pH 2.
Figure 10B:
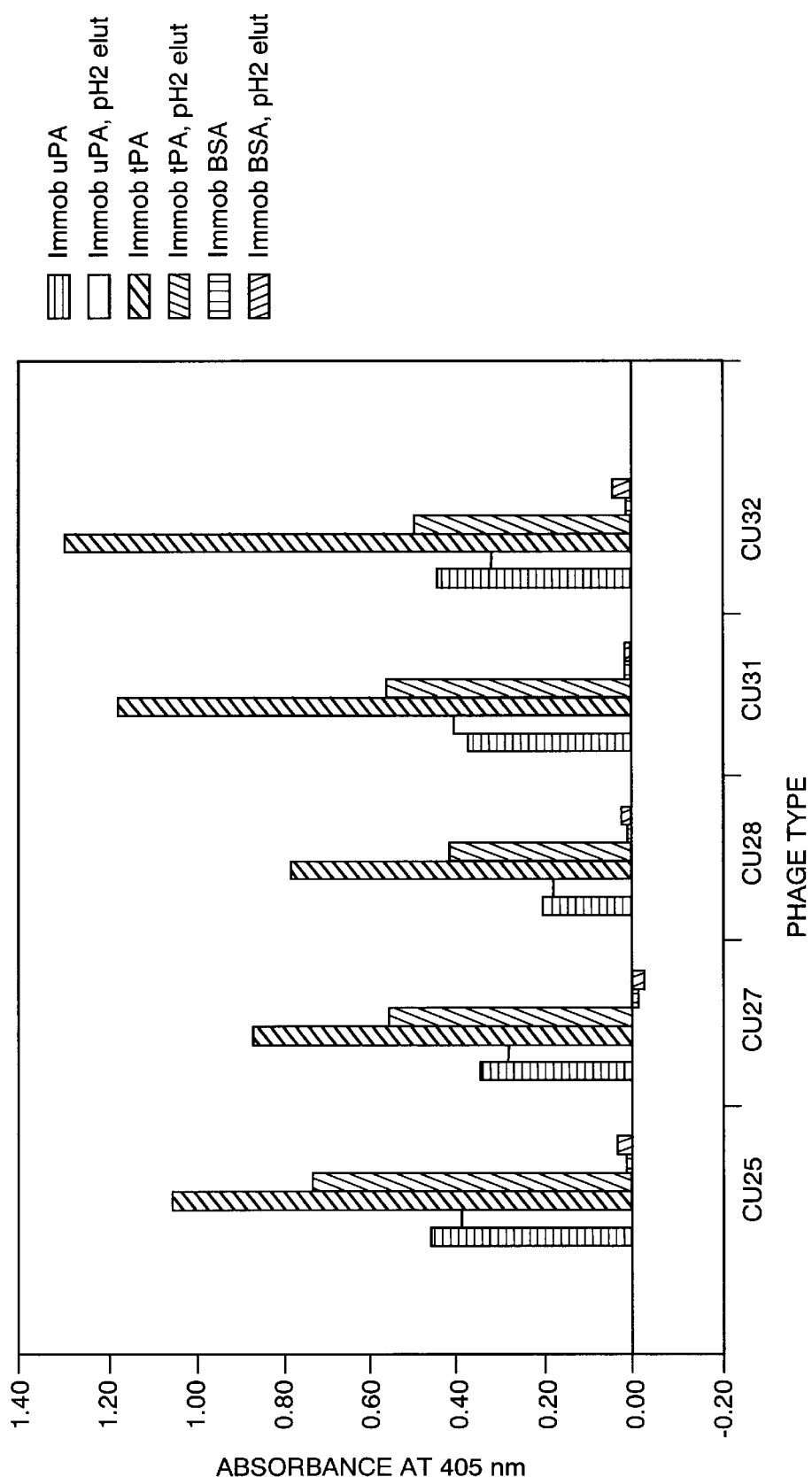
FIG. 10B shows the results of an ELISA testing the binding of some of the CMTI phage isolates having urkinase binding affinity from four rounds of screening: CU25, CU27, CU28, CU 31 and CU32 (see Example 19 infra) against immobilized urokinase at pH 7, immobilized urokinase at pH 2, immobilized tPA at pH 7, immobilized tPA at pH 2, immobilized BSA at pH 7, and immobilized BSA at pH 2. None of these isolates were suitable as an affinity ligand according to the criteria of the test.
Figure 11A:
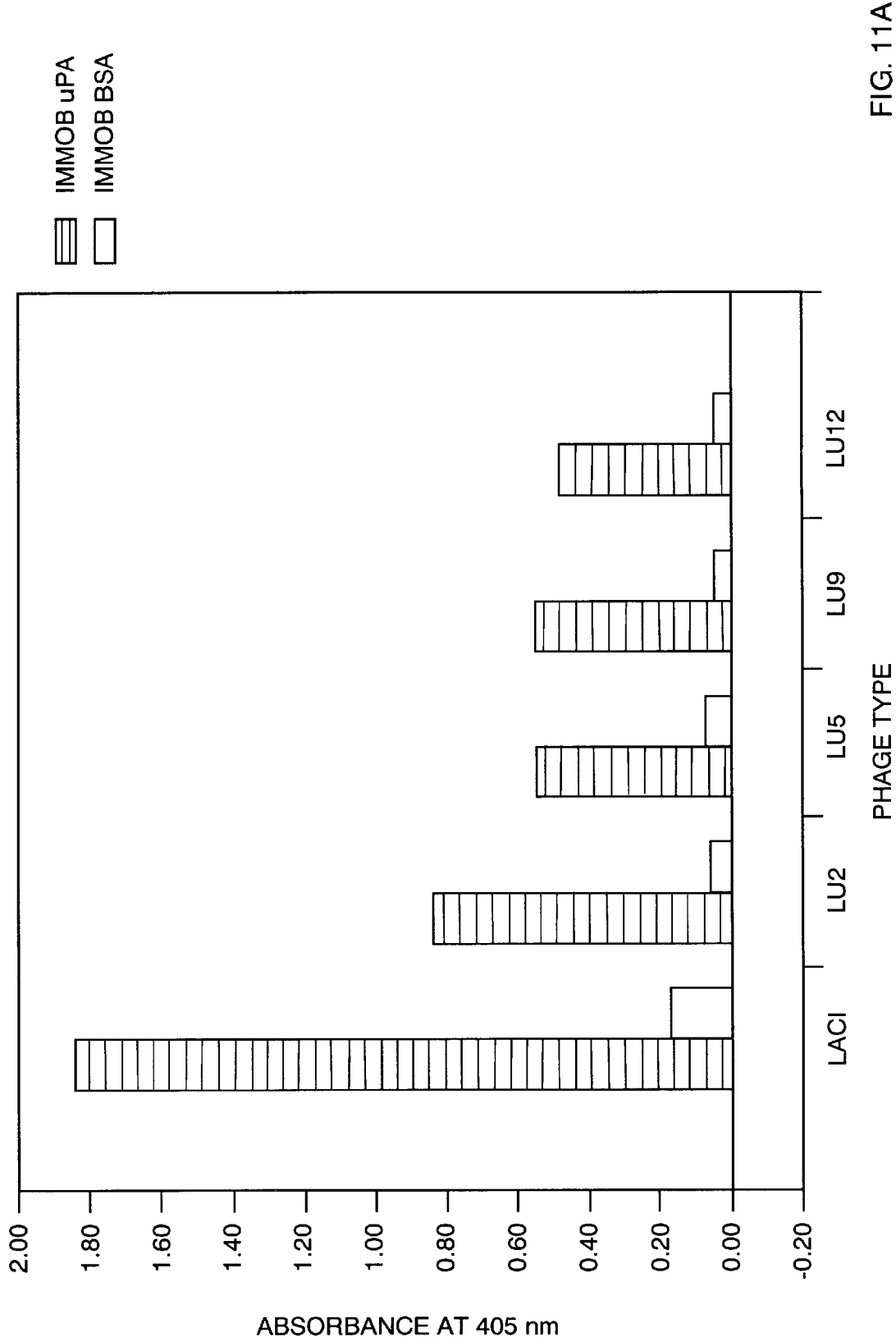
FIG. 11A shows the results of an ELISA testing the binding of some of the LACI/F phage isolates having urkinase binding affinity from four rounds of screening: LU2, LU5, LU9 and LU12 (see Example 19 infra) against immobilized urokinase at pH 7 and immobilized BSA at pH 7.
Figure 11B:
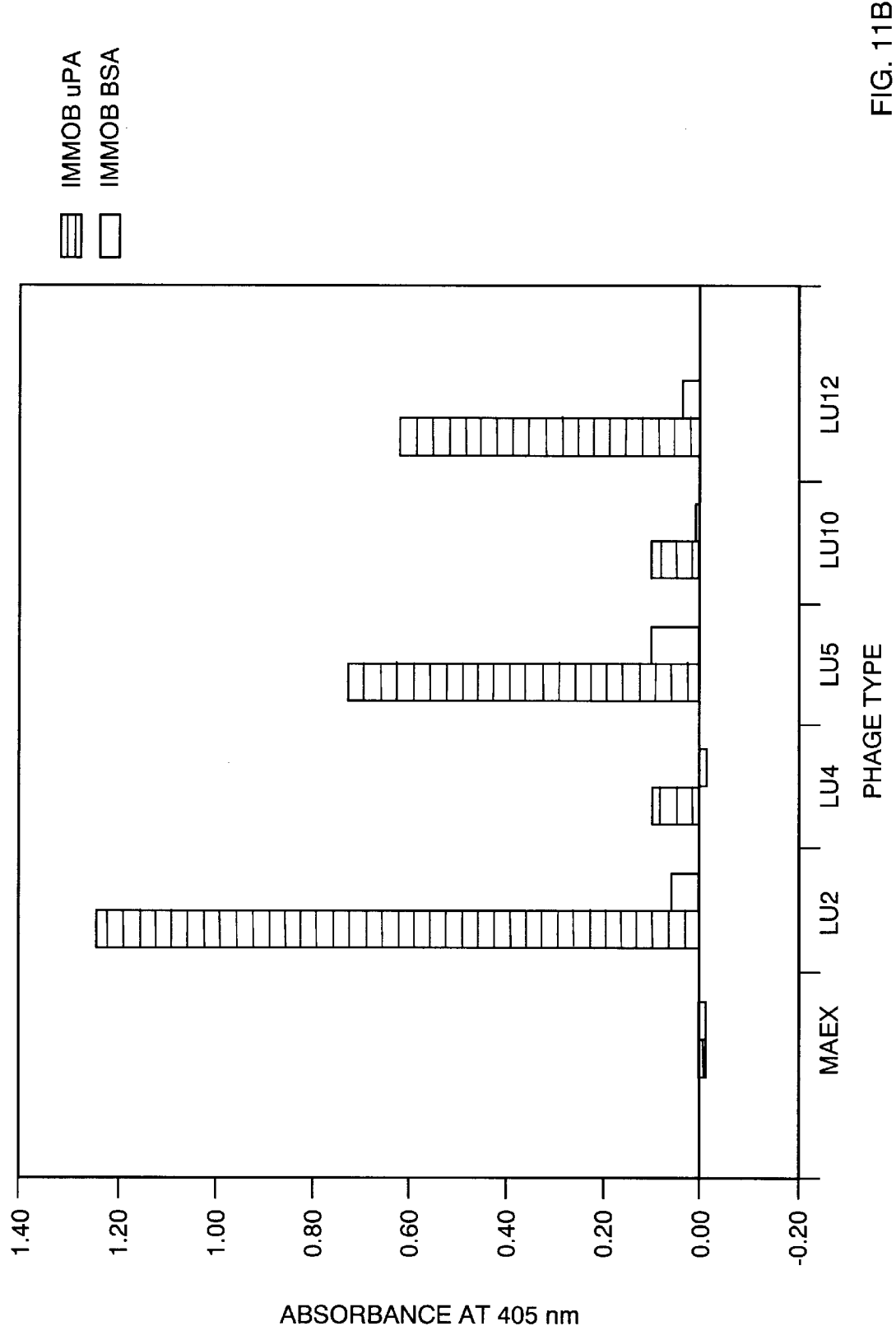
FIG. 11B shows the results of an ELISA testing the binding of some of the LACI/F phage isolates having urkinase binding affinity from four rounds of screening: LU2, LU4, LU10 and LU12 (see Example 19 infra) against immobilized urokinase at pH 7 and immobilized BSA at pH 7. None of these isolates were suitable as an affinity ligand according to the criteria of the test.

Individual isolate phage were tested for binding to immobilized hMAb, goat IgG, or BSA including parental phage controls for hMAb, goat IgG, BSA and anti-M13 binding. Binding to hMAb, goat IgG and BSA was carried out in the presence of 0.5% goat IgG in ½×PBS and 0.1% BSA solution and under two pH conditions, pH 7 and pH 2. The biotinylated detection anti-M13 antibody was visualized using streptavidin-conjugated alkaline phosphatase. The microtiter plates were read at 405 nm in a Bio-Tek microtiter plate reader. The results are shown in FIGS. 5, 6 and 7. In these figures, "CMTI", "MAEX" and "MKTN" are control phage exhibitingthe "parental" candidate binding domain, i.e., the native CMTI-I sequence (SEQ ID NO: 1) for the CMTI control, and randomly selected non-binding members of the TN-6/I (MAEX) and TN-10/V (MKTN) libraries, respectively. A potential affinity ligand was identified by having (1) significantly higher binding affinity for the target hMAb an the control phage, (2) a significantly higher binding affinity for the target under binding conditions (pH 7) than at elution conditions (pH 2), and (3) little or no binding to goat IgG.

From the ELISA results, seven DNA isolates (encoding six binding polypeptides) were suitable for use as affinity ligands: C3, C21, C22, C23 (same amino acid sequence as C22), T42, T49 and T52. The reduction in variability among the CMTI-pH5 isolates and among the TN-6/I pH 2 isolates is shown in Tables 14 and 15 below.

TABLE 14

Reduction in variability at positions in CMTI-I isolates C21, C22, C23, selected for binding to immobilized hMAB

| Position: | 2 | 3 | 4 | 5 | 6 | 7 | 8 | 9 | 10 |
|---|---|---|---|---|---|---|---|---|---|
| Permitted Variability | 13 | C | 15 | 4 | 15 | 15 | 13 | 4 | C |

TABLE 14-continued

Reduction in variability at positions in CMTI-I isolates C21, C22, C23, selected for binding to immobilized hMAB

| Variability of pH 5 Selectants | 2 | C | 2 | 1 | 1 | 1 | 2 | 1 | C |
|---|---|---|---|---|---|---|---|---|---|

TABLE 15

Reduction in variability at positions in TN-6/I isolates T42, T49, T52, selected for binding to immobilized hMAB

| Position: | 4 | 5 | 6 | 7 | 8 | 9 | 10 | 11 |
|---|---|---|---|---|---|---|---|---|
| Permitted Variability | 15 | C | 15 | 13 | 13 | 15 | C | 15 |

TABLE 15-continued

Reduction in variability at positions in TN-6/I isolates T42, T49, T52, selected for binding to immobilized hMAB

| Variability of pH 2 Selectants | 1 | C | 1 | 1 | 3 | 1 | C | 2 |
|---|---|---|---|---|---|---|---|---|

The unity of amino acid types at varied amino acid positions 5, 6, 7 and 9 in the CMTI analogues and at varied positions 4, 6, 7, 9 and 10 in the TN-6/I analogues is an indication of a powerful convergence on a consensus peptide from these libraries. Amplification of these analog-bearing phage, isolation and sequencing of the encoded insert DNA will reveal specific affinity ligand candidates for purification of the hMAb.

EXAMPLE 19

This example illustrates the isolation of affinity ligands useful in separating natural urokinase.

High molecular weight urokinase derived from human urine was immobilized on Reacti-Gel™ agarose beads (Pierce Chemical Co.) at 4° C. essentially as described in Markland et al. (1996).

The screening was carried out using four phage display libraries: CMTI, TN-6/I, TN-10/VIIIa, and LACI/F. The construction of CMTI is given above (Table 7). The construction of TN-6/I is given above (Table 10). The peptide construction of TN-10/VIIIa and LACI/F are set forth below (Tables 16 and 17, respectively). In the following tables, the encoded amino acids of the variegated, phage-displayed polypeptide domain are shown. DNA encoding the polypeptides was inserted into Gene III as described with respect to the CMTI library above (Example 16; Table 7 supra).

TABLE 16

Construction of TN-10/VIIIa Library by Variegation of Microprotein-10 framework sequence: AEGAS C$X_1X_2X_1$P $X_1X_3X_4X_5$C AGP    (SEQ ID NO: 46)
$X_1$ = ACDEFGHIKLMNPQRSTVWY
$X_2$ = AGPR
$X_3$ = AEGLPQRV
$X_4$ = AEGKLMNPQRSTVW
$X_5$ = AGPRSTW

| amino acids encoded (SEQ ID NO: 46) | A | E | G | A | S | C | ACDE FGHI KLM NPQR STV WY | AGPR | ACDE FGHI KLM NPQR STV WY |
|---|---|---|---|---|---|---|---|---|---|
| amino acid position | 1 | 2 | 3 | 4 | 5 | 6 | 7 | 8 | 9 |
| amino acids encoded | P | ACDE FGHI KLM NPQR STV WY | AEGL PQRV | AEGK LMP QRST VW | AGPR STW | C | A | G | P |
| amino acid position | 10 | 11 | 12 | 13 | 14 | 15 | 16 | 17 | 18 |

This library design gives $2.3 \times 10^7$ position and $1.3 \times 10^8$ DNA sequences.

TABLE 17

Construction of LACI/F Library based on the first Kunitz domain of lipoprotein associated coagulation inhibitor framework sequence: MHSFCAFKAD DGPCKAIMKR FFFNIFTRQC EEFIYGGCEG
NQNRFESLEE CKKMCTRD    (SEQ ID NO: 47)

| amino acids encoded (SEQ ID NO: 48) | M | H | S | F | C | A | F | K | A |
|---|---|---|---|---|---|---|---|---|---|
| amino acid position | 1 | 2 | 3 | 4 | 5 | 6 | 7 | 8 | 9 |
| amino acids encoded | D | D | G | PHLR | C | K | AG | IACD FGHL NPRS TVY | MAC DEFG HIKL NPQR STV WY |
| amino acid position | 10 | 11 | 12 | 13 | 14 | 15 | 16 | 17 | 18 |
| amino acids encoded | KAEG LMP QRST | R | F | F | F | N | I | F | T |

TABLE 17-continued

Construction of LACI/F Library based on the first Kunitz domain of lipoprotein associated coagulation inhibitor

| | VW | | | | | | | | |
|---|---|---|---|---|---|---|---|---|---|
| amino acid position | 19 | 20 | 21 | 22 | 23 | 24 | 25 | 26 | 27 |
| amino acids encoded | R | Q | C | E | E | F | I | Y | G |
| amino acid position | 28 | 29 | 30 | 31 | 32 | 33 | 34 | 35 | 36 |
| amino acids encoded | G | C | E | G | N | Q | N | R | F |
| amino acid position | 37 | 38 | 39 | 40 | 41 | 42 | 43 | 44 | 45 |
| amino acids encoded | E | S | L | E | E | C | K | K | M |
| amino acid position | 46 | 47 | 48 | 49 | 50 | 51 | 52 | 53 | 54 |
| amino acids encoded | C | T | R | D | | | | | |
| amino acid position | 55 | 56 | 57 | 58 | | | | | |

Prior to screening, the immobilized urokinase agarose beads were tested with clonally pure phage preps displaying each of the parental binding domain polypeptides, to ensure that under the screening conditions there was a low background level of phage recovered. For each of the parental polypeptides, the fraction of input phage recovered was less than or equeal to $1 \times 10^{-5}$, which was an _acceptably low background level of binding.

Four rounds of screening were performed. Each round consisted of a binding step, a wash procedure, and one or more elution steps. The binding conditions for all rounds were: incubation at 4° C. for 20 hours in PBS, 0.1% BSA, 0.01% Tween 80. The wash and elution conditions for each round are summarized in Table 18.

TABLE 18

Washes and Elution Conditions

| | Screening Round # | | | |
|---|---|---|---|---|
| Step | 1 | 2 | 3 | 4 |
| Wash: 5 times/5 min. at 4° C. with PBS, 0.1% BSA, 0.01% Tween 80 | yes | no | no | no |
| Wash: 5 times/5 min. at 4° C. with PBS, 0.05% Tween 80 | no | yes | yes | yes |
| Elute: 10 min. at RT with 50 mM citrate, 150 mM NaCl, 0.1% BSA, pH 5 | no | yes | yes | yes |
| Elute: 2 times/10 min. at RT with 50 mM citrate, 150 mM NaCl, 0.1% BSA, pH 2 | yes | no | no | no |
| Elute: 10 min. at RT with 50 mM citrate, 150 mM NaCl, 0.1% BSA, pH 5 | no | yes | yes | yes |

After each round, the phage eluted were counted and then amplified by transduction. pH 5 and pH 2 eluates were amplified separately after Round 2 and kept separate during successive screens, so that the pH 2 eluates selected candidates that still had a comparatively high affinity at pH 5. Table 18 below shows the convergence of the screen over the four rounds for each of the libraries.

TABLE 18

Ave. fraction of input phage contained in each round of screening against urokinase

| Round # | TN-6 pH 5 elution | TN-6 pH 2 elution | TN-10 pH 5 elution | TN-10 pH 2 elution | LACI/F pH 5 elution | LACI/F pH 2 elution | CMTI pH 5 elution | CMTI pH 2 elution |
|---|---|---|---|---|---|---|---|---|
| 1 | N/A | $3 \times 10^{-6}$ | N/A | $1 \times 10^{-5}$ | N/A | $4 \times 10^{-6}$ | N/A | $6 \times 10^{-6}$ |
| 2 | $1 \times 10^{-5}$ | $9 \times 10^{-6}$ | $7 \times 10^{-6}$ | $5 \times 10^{-6}$ | $4 \times 10^{-6}$ | $3 \times 10^{-6}$ | $4 \times 10^{-6}$ | $5 \times 10^{-6}$ |
| 3 | $1 \times 10^{-4}$ | $1 \times 10^{-5}$ | $4 \times 10^{-5}$ | $9 \times 10^{-6}$ | $1 \times 10^{-5}$ | $7 \times 10^{-6}$ | $2 \times 10^{-5}$ | $2 \times 10^{-5}$ |
| 4 | $3 \times 10^{-5}$ | $1 \times 10^{-4}$ | $4 \times 10^{-5}$ | $2 \times 10^{-5}$ | $2 \times 10^{-5}$ | $2 \times 10^{-5}$ | $5 \times 10^{-5}$ | $3 \times 10^{-5}$ |

A convergent screen is one in which the fraction of input increases over successive rounds, indicating that the diversity of the phage library is being reduced. This is a desired result, because it indicates that a ligand candidate for the immobilized target molecule is potentially being selected from the population. The table above shows some convergence between Rounds 2 and 4 for all of the libraries, with the most pronounced results for the TN-6/I (pH 2) and the CMTI (pH 5) elutions.

From each of four convergent screens, approximately 12 phage isolates were selected for sequencing. In all of the sequenced isolates, some homology amongst the selectants was seen. The greatest homology was seen in the TN-6/I and CMTI sequences, which is consistent with the finding that these libraries showed the greatest enrichment during screening. For example, nine of the TN-6/I isolates were found to have the same DNA and amino acid sequence.

Candidates were selected for characterization of the relative binding affinity, specificity and pH-release characteristics of the phage-bound proteins for the target, using pH 2 as the release test. The test involved immobilization of urokinase and BSA on Immulon 2 microtiter plates, with detection of relative binding of the phage using a biotinylated sheep anti-M13 antibody ELISA kit from 5 Prime→3 Prime, Inc. (Boulder, Colo. US)

The phage isolates tested had the following designations:

from TN-6/I, pH 2 release: TU33, TU34, TU36, TU37, TU39, TU42 from TN-10/VIIIa, pH 2 release: TU50, TU51, TU53, TU54, TU55, TU56, TU57, TU58, TU60 TU62, TU63 from CMTI, pH 5 release: CU22, CU25, CU27, CU28, CU29, CU31, CU32 from LACI/F, pH 2 release: LU2, LU4, LU5, LU9, LU10, LU12

Individual isolate phage were tested for binding to immobilized urokinase or BSA. Because urokinase has a high sequence homology to tPA, the candidates also were tested for tPA binding. The results are shown in FIGS. 8, 9, 10 and 11. A potential affinity ligand was identified by having (1) significantly higher binding affinity for the target urokinase than the control phage, (2) a significantly higher binding affinity for the target under binding conditions (pH 7) than at elution conditions (pH 2), and (3) little or no binding to BSA.

From the ELISA results, seven DNA isolates (four from TN-6/I and three from TN-10/VIIIa) were suitable for use as affinity ligands: TU33, TU36, TU39, TU42, TU53, TU56 and TU58. All seven isolates exhibited high affinity at pH 7 for urokinase and reduced affinity at pH 2. No ligand candidates were discovered from the CMTI or LACI/F libraries that bound with higher affinity to urokinase than the parenwal display phage. The reduction in variability among the CMT- pH5 isolates and amonge the TN-6/I pH 2 isolates is shown in Tables 21 and 22 below.

TABLE 21

Reduction in variability at positions in TN-6/I isolates TU33, TU36, TU39 and TU42 selected for binding to immobilized urokinase

| Position: | 4 | 5 | 6 | 7 | 8 | 9 | 10 | 11 |
|---|---|---|---|---|---|---|---|---|
| Permitted Variability | 15 | C | 15 | 13 | 13 | 15 | C | 15 |
| Variability of pH 2 Selectants | 3 | C | 2 | 1 | 1 | 2 | C | 1 |

TABLE 22

Reduction in variability at positions in TN-10/VIIIa TU53, TU56 and TU58 selected for binding to immobilized urokinase

| Position: | 6 | 7 | 8 | 9 | 10 | 11 | 12 | 13 | 14 | 15 |
|---|---|---|---|---|---|---|---|---|---|---|
| Permitted Variability | C | 20 | 4 | 20 | P | 20 | 8 | 13 | 7 | C |
| Variability of pH 2 Selectants | C | 3 | 2 | 3 | P | 2 | 3 | 2 | 1 | C |

The unity of amino acid types at varied amino acid positions 7, 8 and 11 in the TN-6/I analogues and the sharp reduction in amino acid variability at varied positions 7, 9, 11 and 14 in the TN-10/VIIIa analogues is an indication of a powerfuil convergence on a consensus peptide from these libraries. Amplification of these analog-bearing phage, isolation and sequencing of the encoded insert DNA will reveal specific affinity ligand candidates for urokinase purification.

Following the foregoing description, the characteristic important for the separation of a target from any feed stream can be engineered into the binding domains of a designed library, so that the method of his invention invariably leads to several affinity ligand candidates suitable for separation of the target under desirable conditions of binding and release. High yield of the target without inactivation or disruption of the product, with high purity, with the elimination of even closedly related impurities, at acceptable cost and with re-usable or recyclable materials all can be achieved according to the present invention. Additional embodiments of the invention and alternative methods adapted to a particular target will be evident from studying the foregoing description. All such embodiments and alternatives are intended to be within the scope of this invention, as defined by the claims that follow.

REFERENCES

Boschetti, E., *J. Chromatography*, A 658: 207–236 (1994).
Ladner, R. C., "Constrained peptides as binding entities," *Trends in Biotechnology*, 13(10): 426–430 (1995).
Markland, W., Roberts, B. L., Ladner, R. C., "Selection for Protease Inhibitors Using Bacteriophage Display," *Methods in Enzymology*, 267: 28–51 (1996).
Narayanan, S. R., "Preparative affinity chromatography of proteins," *J. Chrom.* A, 658: 237–258 (1994).
Knight, P., *Bio/Technology*, 8: 200 (1990).
Vedvick, T., Buckholtz, R. G., Engel, M., Urcam, M., Kinney, S., Provow, S., Siegel, R. S., and Thill, G. P., "High level secretion of biologically active aprotinin from the yeast *Pichia pastoris*", *J. Industrial Microbiol.*, 7: 197–202 (1991).
Wagner, S. L., Siegel, R. S., Vedvick, T. S., Raschke, W. C., and Van Nostrand, W.E., "High level expression, purification, and characterization of the Kunitz-type protease inhibitor domain of protease Nexin-2/amyloid β-protein precursor," *Biochem. Biphys. Res. Comm.*, 186: 1138–1145 (1992).

What is claimed is:

1. A method for isolating an affinity ligand suitable for separating a target molecule from a solution containing said target molecule, wherein said affinity ligand is a polypeptide, the method comprising:
   (a) selecting, with respect to the target molecule, a first solution condition at which an affinity ligand will bind to said target molecule and at which the target molecule is not denatured;
   (b) selecting, with respect to the target molecule, a second solution condition at which the affinity ligand will not bind to said target molecule and at which the target molecule is not denatured, wherein said second solution condition is different from said first solution condition;
   (c) providing a lebrary of polypeptides;
   (d) contacting said library of polypeptides with said target molecule at the first solution condition, for sufficient time to permit polypeptide/target binding complexes to form;
   (e) removing polypeptides that do not bind the target under the first solution condition;
   (f) altering the first solution condition of contacting step (d) to the second solution condition; and (g) recovering polypeptides that release the target molecule under the second solution condition, wherein the recovered polypeptides identify isolated affinity ligands that bind said target molecule under said first solution condition and do not bind said target molecule under said second solution condition.

2. The method of claim 1, wherein, as a preliminary step of said method, a range of stability for the target molecule in the solution containing it is ascertained with respect to two or more parameters selected from temperature, pH, ionic strength, dielectric constant, concentration of solutes, presence or absence of metal ions, and presence or absence of metal chelating agents, thereby defining a stability envelope for said target molecule, wherein said first and second solution conditions are within said stability envelope.

3. The method of claim 2, wherein said stability envelope is defined by a range of pH, a salt concentration range, and a concentration range for urea or EDTA.

4. The method of claim 1, wherein the target molecule is not denatured under the conditions:

1) a range of pH 2–pH 11,
2) a range of 1 mM–250 mM NaCl, and
3) a range of 4° C.–40° C.;

said first solution condition is at pH 7, 150 mM NaCl, and 22° C.; and said second solution condition is at pH5, 150 mM NaCl and 22° C.

5. The method of claim 1, wherein said library of polypeptides is prepared by inserting a synthetic DNA encoding each polypeptide in a replicable genetic package, resulting, on expression, in display of an analogue binding domain on the surface of said genetic package.

6. The method of claim 5, wherein said replicable genetic package is a bacteriophage.

7. The method of claim 6, wherein said bacteriophage is M13 and said synthetic DNA is inserted in gene iii.

8. A method for obtaining DNA encoding an engincered affinity ligand that binds to a target molecule with a high degree of specificity under a first binding condition and releases from the target molecule under a second condition, comprsing:

(a) obtaining one or more affinity ligands expressed on the surface of a replicable genetic package according to the method of claim 5,
(b) allowing said genetic package to multiply, and
(c) isolating DNA corresponding to the synthetic DNA from said multiplied genetic packages.

9. A method for obtaining a substantially pure engineered affinity ligand, comprising (a) expressing the isolated synthetic DNA obtained by the method of claim 8 in a gene expression system to produce an engineered affinity ligand, and
(b) recovering said engineered affinity ligand.

10. The method of claim 1, wherein the target is immobilized prior to said contacting step (d).

* * * * *

UNITED STATES PATENT AND TRADEMARK OFFICE
CERTIFICATE OF CORRECTION

PATENT NO. : 6,326,155 B1
DATED : December 4, 2001
INVENTOR(S) : Maclennan and Ladner It is certified that error appears in the above-identified patent and that said Letters Patent is hereby corrected as shown below:

<u>Title page,</u>
Item [63], "Mar. 20, 1995, now abandoned" should read -- Mar. 20, 1996, now abandoned --

<u>Column 66,</u>
Line 59, "lebrary" should read -- library --.

<u>Column 68,</u>
Line 8, "engincered" should read -- engineered --.

Signed and Sealed this

Eighth Day of April, 2003

JAMES E. ROGAN
*Director of the United States Patent and Trademark Office*

SEQUENCE LISTING (1) GENERAL INFORMATION:

(iii) NUMBER OF SEQUENCES:48

(2) INFORMATION FOR SEQ ID NO:1:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

Arg Val Cys Pro Arg Ile Leu Met Glu Cys Lys Lys Asp Ser Asp Cys
  1               5                  10                  15

Leu Ala Glu Cys Val Cys Leu Glu His Gly Tyr Cys Gly
             20                  25

(2) INFORMATION FOR SEQ ID NO:2:

(i) SEQUENCE CHARACTERISTICS:
        (A) LENGTH:50 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Phe Tyr Ser Gly Ala Arg Xaa Cys Xaa Xaa Xaa Xaa Xaa Xaa Cys Lys
 -5                   1               5                  10

Lys Asp Ser Asp Cys Leu Ala Glu Cys Val Cys Leu Glu His Gly Tyr
                 15                  20                  25

Cys Gly Ala Gly Pro Ser Tyr Ile Glu Gly Arg Ile Val Gly Ser Ala
             30                  35                  40

Ala Glu
     45

(2) INFORMATION FOR SEQ ID NO:3:

(i) SEQUENCE CHARACTERISTICS:
        (A) LENGTH:150 bases
        (B) TYPE: nucleic acid
        (C) STRANDEDNESS: single
        (D) TOPOLOGY: linear (ii) MOLECULE TYPE:other nucleic acid
        (A) DESCRIPTION:synthetic DNA fragment (xi) SEQUENCE DESCRIPTION: SEQ ID NO:3:

TTCTATTCCG GAGCCCGTNN GTGTNNTANA NNTNNTNNGR RGTGTAAGAA               50

GGATTCTGAT TGCTTAGCAG AATGCGTTTG CCTCGAGCAT GGTTATTGTG              100

GCGCCGGTCC TTCATACATT GAAGGTCGTA TTGTCGGTAG CGCCGCTGAA              150

(2) INFORMATION FOR SEQ ID NO:4:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Arg Trp Cys Pro Lys Thr Ser Leu Gly Cys Met Lys Asp Ser Asp Cys
1               5                   10                  15

Leu Ala Glu Cys Val Cys Leu Glu His Gly Tyr Cys Gly
            20                  25

(2) INFORMATION FOR SEQ ID NO:5:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Arg Leu Cys Pro Lys Thr Tyr Leu Gly Cys Met Lys Asp Ser Asp Cys
1               5                   10                  15

Leu Ala Glu Cys Val Cys Leu Glu His Gly Tyr Cys Gly
            20                  25

(2) INFORMATION FOR SEQ ID NO:6:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Arg Trp Cys Ser Thr Tyr Ser Leu Gly Cys Met Lys Asp Ser Asp Cys
1               5                   10                  15

Leu Ala Glu Cys Val Cys Leu Glu His Gly Tyr Cys Gly
            20                  25

(2) INFORMATION FOR SEQ ID NO:7:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Arg Trp Cys Ser Thr Tyr Ser Leu Gly Cys Met Lys Asp Ser Asp Cys
1               5                   10                  15

Leu Ala Glu Cys Val Cys Leu Glu His Gly Tyr Cys Gly
            20                  25

(2) INFORMATION FOR SEQ ID NO:8:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Arg Leu Cys Pro Lys Thr Ser Leu Glu Cys Met Lys Asp Ser Asp Cys
 1               5                  10                  15
Leu Ala Glu Cys Val Cys Leu Glu His Gly Tyr Cys Gly
            20                  25

(2) INFORMATION FOR SEQ ID NO:9:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Arg Trp Cys Ser Thr Tyr Ser Leu Gly Cys Met Lys Asp Ser Asp Cys
 1               5                  10                  15
Leu Ala Glu Cys Val Cys Leu Glu His Gly Tyr Cys Gly
            20                  25

(2) INFORMATION FOR SEQ ID NO:10:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Arg Leu Cys Pro Lys Thr Ser Leu Glu Cys Met Lys Asp Ser Asp Cys
 1               5                  10                  15
Leu Ala Glu Cys Val Cys Leu Glu His Gly Tyr Cys Gly
            20                  25

(2) INFORMATION FOR SEQ ID NO:11:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Arg Trp Cys Ser Lys Ser Ser Leu Glu Cys Met Lys Asp Ser Asp Cys
 1               5                  10                  15
Leu Ala Glu Cys Val Cys Leu Glu His Gly Tyr Cys Gly
            20                  25

(2) INFORMATION FOR SEQ ID NO:12:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Arg Leu Cys Pro Lys Thr Asp Leu Gly Cys Met Lys Asp Ser Asp Cys

```
                1               5              10              15
Leu Ala Glu Cys Val Cys Leu Glu His Gly Tyr Cys Gly
                20                      25

(2) INFORMATION FOR SEQ ID NO:13:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Arg Trp Cys Pro Lys Ser Ser Met Gly Cys Lys Lys Asp Ser Asp Cys
 1               5                      10                      15
Leu Ala Glu Cys Val Cys Leu Glu His Gly Tyr Cys Gly
                20                      25

(2) INFORMATION FOR SEQ ID NO:14:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Arg Trp Cys Pro Arg Thr Val Gln Glu Cys Met Lys Asp Ser Asp Cys
 1               5                      10                      15
Leu Ala Glu Cys Val Cys Leu Glu His Gly Tyr Cys Gly
                20                      25

(2) INFORMATION FOR SEQ ID NO:15:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

Arg Trp Cys Pro Thr Ala Pro Leu Glu Cys Met Lys Asp Ser Asp Cys
 1               5                      10                      15
Leu Ala Glu Cys Val Cys Leu Glu His Gly Tyr Cys Gly
                20                      25

(2) INFORMATION FOR SEQ ID NO:16:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

Arg Leu Cys Pro Lys Thr Asp Leu Gly Cys Met Lys Asp Ser Asp Cys
 1               5                      10                      15
Leu Ala Glu Cys Val Cys Leu Glu His Gly Tyr Cys Gly
```

20          25

(2) INFORMATION FOR SEQ ID NO:17:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

Arg Trp Cys Pro Lys Ser Ala Leu Asp Cys Lys Lys Asp Ser Asp Cys
 1               5                  10                  15

Leu Ala Glu Cys Val Cys Leu Glu His Gly Tyr Cys Gly
            20                  25

(2) INFORMATION FOR SEQ ID NO:18:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

Arg Trp Cys Thr Lys Thr Ser Arg Glu Cys Met Lys Asp Ser Asp Cys
 1               5                  10                  15

Leu Ala Glu Cys Val Cys Leu Glu His Gly Tyr Cys Gly
            20                  25

(2) INFORMATION FOR SEQ ID NO:19:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

Arg Trp Cys Ile Arg Thr Asp Leu Gly Cys Met Lys Asp Ser Asp Cys
 1               5                  10                  15

Leu Ala Glu Cys Val Cys Leu Glu His Gly Tyr Cys Gly
            20                  25

(2) INFORMATION FOR SEQ ID NO:20:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

Arg Trp Cys Pro Lys Thr Ser Leu Gly Cys Met Lys Asp Ser Asp Cys
 1               5                  10                  15

Leu Ala Glu Cys Val Cys Leu Glu His Gly Tyr Cys Gly
            20                  25

(2) INFORMATION FOR SEQ ID NO:21:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

Arg Trp Cys Pro Arg Thr Val Arg Arg Cys Met Lys Asp Ser Asp Cys
1               5                   10                  15

Leu Ala Glu Cys Val Cys Leu Glu His Gly Tyr Cys Gly
            20                  25

(2) INFORMATION FOR SEQ ID NO:22:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

Arg Trp Cys Pro Lys Thr His Lys Glu Cys Met Lys Asp Ser Asp Cys
1               5                   10                  15

Leu Ala Glu Cys Val Cys Leu Glu His Gly Tyr Cys Gly
            20                  25

(2) INFORMATION FOR SEQ ID NO:23:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

Arg Trp Cys Pro Lys Thr Ser Leu Glu Cys Met Lys Asp Ser Asp Cys
1               5                   10                  15

Leu Ala Glu Cys Val Cys Leu Glu His Gly Tyr Cys Gly
            20                  25

(2) INFORMATION FOR SEQ ID NO:24:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:24:

Arg Trp Cys Pro Lys Ser Thr Leu Gly Cys Met Lys Asp Ser Asp Cys
1               5                   10                  15

Leu Ala Glu Cys Val Cys Leu Glu His Gly Tyr Cys Gly
            20                  25

(2) INFORMATION FOR SEQ ID NO:25:

(i) SEQUENCE CHARACTERISTICS:

(A) LENGTH:29 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:25:

Arg Trp Cys Pro Lys Ser Thr Leu Gly Cys Met Lys Asp Ser Asp Cys
 1               5                  10                  15

Leu Ala Glu Cys Val Cys Leu Glu His Gly Tyr Cys Gly
            20                  25

(2) INFORMATION FOR SEQ ID NO:26:

(i) SEQUENCE CHARACTERISTICS:
            (A) LENGTH:29 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:26:

Arg Trp Cys Pro Lys Tyr Thr Leu Glu Cys Met Lys Asp Ser Asp Cys
 1               5                  10                  15

Leu Ala Glu Cys Val Cys Leu Glu His Gly Tyr Cys Gly
            20                  25

(2) INFORMATION FOR SEQ ID NO:27:

(i) SEQUENCE CHARACTERISTICS:
            (A) LENGTH:29 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:27:

Arg Trp Cys Pro Arg Ser Ser Leu Glu Cys Met Lys Asp Ser Asp Cys
 1               5                  10                  15

Leu Ala Glu Cys Val Cys Leu Glu His Gly Tyr Cys Gly
            20                  25

(2) INFORMATION FOR SEQ ID NO:28:

(i) SEQUENCE CHARACTERISTICS:
            (A) LENGTH:29 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:28:

Arg Trp Cys Pro Lys Tyr Thr Leu Glu Cys Met Lys Asp Ser Asp Cys
 1               5                  10                  15

Leu Ala Glu Cys Val Cys Leu Glu His Gly Tyr Cys Gly
            20                  25

(2) INFORMATION FOR SEQ ID NO:29:

(i) SEQUENCE CHARACTERISTICS:
            (A) LENGTH:29 amino acids
            (B) TYPE: amino acid
            (C) STRANDEDNESS: single (D) TOPOLOGY: linear (ii) MOLECULE TYPE: protein (xi) SEQUENCE DESCRIPTION: SEQ ID NO:29:

Arg Trp Cys Pro Arg Ser Asn Leu Glu Cys Met Lys Asp Ser Asp Cys
 1               5                  10                  15

Leu Ala Glu Cys Val Cys Leu Glu His Gly Tyr Cys Gly
            20                  25

(2) INFORMATION FOR SEQ ID NO:30:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

Arg Trp Cys Pro Arg Ser Asn Leu Glu Cys Met Lys Asp Ser Asp Cys
 1               5                  10                  15

Leu Ala Glu Cys Val Cys Leu Glu His Gly Tyr Cys Gly
            20                  25

(2) INFORMATION FOR SEQ ID NO:31:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

Arg Trp Cys Pro Lys Tyr Thr Leu Glu Cys Met Lys Asp Ser Asp Cys
 1               5                  10                  15

Leu Ala Glu Cys Val Cys Leu Glu His Gly Tyr Cys Gly
            20                  25

(2) INFORMATION FOR SEQ ID NO:32:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

Arg Trp Cys Pro Lys Tyr Thr Leu Glu Cys Met Lys Asp Ser Asp Cys
 1               5                  10                  15

Leu Ala Glu Cys Val Cys Leu Glu His Gly Tyr Cys Gly
            20                  25

(2) INFORMATION FOR SEQ ID NO:33:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

Arg Trp Cys Pro Lys Tyr Thr Leu Glu Cys Met Lys Asp Ser Asp Cys
 1               5                  10                  15

Leu Ala Glu Cys Val Cys Leu Glu His Gly Tyr Cys Gly
            20                  25

(2) INFORMATION FOR SEQ ID NO:34:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

Arg Trp Cys Pro Arg Ser Thr Leu Glu Cys Met Lys Asp Ser Asp Cys
 1               5                  10                  15

Leu Ala Glu Cys Val Cys Leu Glu His Gly Tyr Cys Gly
            20                  25

(2) INFORMATION FOR SEQ ID NO:35:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

Arg Trp Cys Pro Lys Thr Ser Leu Gly Cys Met Lys Asp Ser Asp Cys
 1               5                  10                  15

Leu Ala Glu Cys Val Cys Leu Glu His Gly Tyr Cys Gly
            20                  25

(2) INFORMATION FOR SEQ ID NO:36:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:36:

Arg Trp Cys Pro Lys Tyr Thr Leu Glu Cys Met Lys Asp Ser Asp Cys
 1               5                  10                  15

Leu Ala Glu Cys Val Cys Leu Glu His Gly Tyr Cys Gly
            20                  25

(2) INFORMATION FOR SEQ ID NO:37:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:37:

```
Arg Trp Cys Pro Arg Ser Ser Leu Glu Cys Met Lys Asp Ser Asp Cys
  1               5                  10                  15
Leu Ala Glu Cys Val Cys Leu Glu His Gly Tyr Cys Gly
             20                  25
```

(2) INFORMATION FOR SEQ ID NO:38:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:38:

```
Arg Trp Cys Pro Lys Ser Thr Leu Gly Cys Met Lys Asp Ser Asp Cys
  1               5                  10                  15
Leu Ala Glu Cys Val Cys Leu Glu His Gly Tyr Cys Gly
             20                  25
```

(2) INFORMATION FOR SEQ ID NO:39:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:39:

```
Arg Trp Cys Pro Arg Ser Ser Leu Glu Cys Met Lys Asp Ser Asp Cys
  1               5                  10                  15
Leu Ala Glu Cys Val Cys Leu Glu His Gly Tyr Cys Gly
             20                  25
```

(2) INFORMATION FOR SEQ ID NO:40:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:40:

```
Arg Trp Cys Pro Arg Ser Asn Leu Glu Cys Met Lys Asp Ser Asp Cys
  1               5                  10                  15
Leu Ala Glu Cys Val Cys Leu Glu His Gly Tyr Cys Gly
             20                  25
```

(2) INFORMATION FOR SEQ ID NO:41:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:

```
Arg Trp Cys Pro Arg Ser Asn Leu Glu Cys Met Lys Asp Ser Asp Cys
  1               5                  10                  15
```

```
Leu Ala Glu Cys Val Cys Leu Glu His Gly Tyr Cys Gly
            20                  25

(2) INFORMATION FOR SEQ ID NO:42:

(i) SEQUENCE CHARACTERISTICS:
        (A) LENGTH:29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:42:

Arg Xaa Cys Xaa Xaa Xaa Xaa Xaa Cys Xaa Lys Asp Ser Asp Cys
                5                   10                  15
Leu Ala Glu Cys Val Cys Leu Glu His Gly Tyr Cys Gly
            20                  25

(2) INFORMATION FOR SEQ ID NO:43:

(i) SEQUENCE CHARACTERISTICS:
        (A) LENGTH:11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:43:

Arg Xaa Cys Xaa Xaa Xaa Xaa Xaa Cys Xaa
                5                   10

(2) INFORMATION FOR SEQ ID NO:44:

(i) SEQUENCE CHARACTERISTICS:
        (A) LENGTH:13 amino acides
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:44:

Ala Glu Gly Xaa Cys Xaa Xaa Xaa Xaa Cys Xaa Ser Tyr
 1               5                   10

(2) INFORMATION FOR SEQ ID NO:45:

(i) SEQUENCE CHARACTERISTICS:
        (A) LENGTH:18 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:45:

Ala Glu Gly Ala Xaa Cys Xaa Xaa Xaa Xaa Xaa Xaa Xaa Xaa Cys Xaa
 1               5                   10                  15
Gly Pro
    18

(2) INFORMATION FOR SEQ ID NO:46:

(i) SEQUENCE CHARACTERISTICS:
        (A) LENGTH:18 amino acids
        (B) TYPE: amino acid
```

```
            (C) STRANDEDNESS: single
            (D) TOPOLOGY: linear (ii) MOLECULE TYPE: protein (xi) SEQUENCE DESCRIPTION: SEQ ID NO:46:

Ala Glu Gly Ala Ser Cys Xaa Xaa Xaa Pro Xaa Xaa Xaa Xaa Cys Ala
 1               5                  10                  15

Gly Pro
    18

(2) INFORMATION FOR SEQ ID NO:47:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:47:

Met His Ser Phe Cys Ala Phe Lys Ala Asp Asp Gly Pro Cys Lys Ala
 1               5                  10                  15

Ile Met Lys Arg Phe Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
                35                  40                  45

Glu Glu Cys Lys Lys Met Cys Thr Arg Asp
    50                  55

(2) INFORMATION FOR SEQ ID NO:48:

(i) SEQUENCE CHARACTERISTICS:
        (A) LENGTH:58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:48:

Met His Ser Phe Cys Ala Phe Lys Ala Asp Asp Gly Xaa Cys Lys Xaa
 1               5                  10                  15

Xaa Xaa Xaa Arg Phe Phe Phe Asn Ile Phe Thr Arg Gln Cys Glu Glu
                20                  25                  30

Phe Ile Tyr Gly Gly Cys Glu Gly Asn Gln Asn Arg Phe Glu Ser Leu
                35                  40                  45

Glu Glu Cys Lys Lys Met Cys Thr Arg Asp
    50                  55
```